United States Patent
Chen et al.

(10) Patent No.: US 10,093,646 B2
(45) Date of Patent: Oct. 9, 2018

(54) 1-PYRIDAZIN-/TRIAZIN-3-YL-PIPER(-AZINE)/IDINE/PYROLIDINE DERIVATIVES AND COMPOSITIONS THEREOF FOR INHIBITING THE ACTIVITY OF SHP2

(71) Applicants: Christine Hiu-Tung Chen, Waltham, MA (US); Zhuoliang Chen, Belmont, MA (US); Jorge Garcia Fortanet, Somerville, MA (US); Denise Grunenfelder, Pasadena, CA (US); Rajesh Karki, Quincy, MA (US); Mitsunori Kato, Cambridge, MA (US); Matthew J. LaMarche, Reading, MA (US); Lawrence Blas Perez, Hopkinton, MA (US); Travis Matthew Stams, Stow, MA (US); Sarah Williams, Emeryville, CA (US)

(72) Inventors: Christine Hiu-Tung Chen, Waltham, MA (US); Zhuoliang Chen, Belmont, MA (US); Jorge Garcia Fortanet, Somerville, MA (US); Denise Grunenfelder, Pasadena, CA (US); Rajesh Karki, Quincy, MA (US); Mitsunori Kato, Cambridge, MA (US); Matthew J. LaMarche, Reading, MA (US); Lawrence Blas Perez, Hopkinton, MA (US); Travis Matthew Stams, Stow, MA (US); Sarah Williams, Emeryville, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/110,498

(22) PCT Filed: Jan. 16, 2015

(86) PCT No.: PCT/IB2015/050343
§ 371 (c)(1),
(2) Date: Jul. 8, 2016

(87) PCT Pub. No.: WO2015/107493
PCT Pub. Date: Jul. 23, 2015

(65) Prior Publication Data
US 2017/0204080 A1 Jul. 20, 2017

Related U.S. Application Data

(60) Provisional application No. 61/928,738, filed on Jan. 17, 2014.

(51) Int. Cl.
C07D 401/04 (2006.01)
C07D 409/14 (2006.01)
(Continued)

(52) U.S. Cl.
CPC ......... C07D 401/04 (2013.01); C07D 401/14 (2013.01); C07D 409/14 (2013.01); C07D 471/04 (2013.01); C07D 487/04 (2013.01)

(58) Field of Classification Search
CPC .. C07D 401/04; C07D 401/14; C07D 403/04; C07D 409/14; C07D 471/04; C07D 487/04
See application file for complete search history.

(56) References Cited

U.S. PATENT DOCUMENTS

| 4,613,603 A | 9/1986 | Biziere et al. |
| 2003/0171359 A1 | 9/2003 | Dahmann et al. |

(Continued)

FOREIGN PATENT DOCUMENTS

| CN | 102753177 A | 10/2012 |
| EP | 799617 A2 | 10/1997 |

(Continued)

OTHER PUBLICATIONS

Whelligan, et al., "Aminopyrazine Inhibitors Binding to an Unusual Inactive Conformation of the Mitotic Kinase Nek2: SAR and Structural Characterization", Journal of Medicinal Chemistry, 2010, vol. 53, No. 21, pp. 7682-7698, American Chemical Society.

(Continued)

*Primary Examiner* — Erich A Leeser
(74) *Attorney, Agent, or Firm* — Scott W. Reid

(57) ABSTRACT

The present invention relates to compounds of formula I:

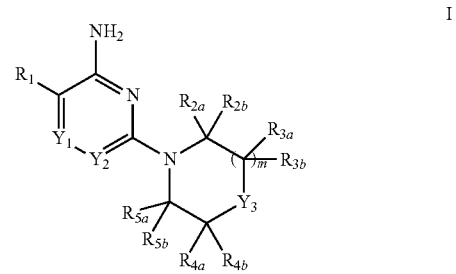

in which m, $Y_1$, $Y_2$, $Y_3$, $R_1$, $R_{2a}$, $R_{2b}$, $R_{3a}$, $R_{3b}$, $R_{4a}$, $R_{4b}$, $R_{5a}$ and $R_{5b}$ are defined in the Summary of the Invention; capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

10 Claims, No Drawings

Specification includes a Sequence Listing.

(51) Int. Cl.
*C07D 471/04* (2006.01)
*C07D 403/04* (2006.01)
*C07D 401/14* (2006.01)
*C07D 487/04* (2006.01)

(56) References Cited

U.S. PATENT DOCUMENTS

| | | |
|---|---|---|
| 2005/0222159 A1 | 10/2005 | Tsutsumi et al. |
| 2008/0024964 A1 | 1/2008 | Lev et al. |
| 2011/0306606 A1 | 12/2011 | Ryu et al. |
| 2011/0319381 A1 | 12/2011 | Abouabdellah et al. |
| 2012/0252818 A1 | 10/2012 | Chiosis et al. |
| 2013/0116430 A1 | 5/2013 | Fujiwara et al. |
| 2015/0315207 A1 | 11/2015 | Morales et al. |

FOREIGN PATENT DOCUMENTS

| | | | |
|---|---|---|---|
| WO | 1991019305 A1 | 5/1991 | |
| WO | 2000059893 A1 | 10/2000 | |
| WO | 2002024679 A1 | 3/2002 | |
| WO | 2005117909 A2 | 12/2005 | |
| WO | 2007031529 A1 | 3/2007 | |
| WO | 2008055959 A1 | 5/2008 | |
| WO | 2008100412 A1 | 8/2008 | |
| WO | 2008110611 A1 | 9/2008 | |
| WO | 2009131687 A2 | 10/2009 | |
| WO | 2009150230 A1 | 12/2009 | |
| WO | 2009158571 A1 | 12/2009 | |
| WO | 2010008739 A2 | 1/2010 | |
| WO | 2010048149 A2 | 4/2010 | |
| WO | 2012121212 A2 | 10/2010 | |
| WO | 2011078143 A1 | 6/2011 | |
| WO | 11022440 A2 | 8/2011 | |
| WO | 2012009217 A1 | 1/2012 | |
| WO | 2012016217 A1 | 2/2012 | |
| WO | 2012027495 A1 | 3/2012 | |
| WO | 2012052948 A1 | 4/2012 | |
| WO | 2013040044 A1 | 3/2013 | |
| WO | 2013096093 A1 | 6/2013 | |
| WO | 2013182546 A1 | 12/2013 | |
| WO | 2014054053 A1 | 4/2014 | |
| WO | 2014160521 A1 | 10/2014 | |
| WO | WO 2015/092819 * | 12/2014 | ......... C07D 253/075 |
| WO | 2015107494 A1 | 7/2015 | |
| WO | 2015107495 A1 | 7/2015 | |
| WO | 2015168466 A1 | 11/2015 | |
| WO | 2016203404 A1 | 12/2016 | |
| WO | 2016203405 A1 | 12/2016 | |
| WO | 2016203406 A1 | 12/2016 | |

OTHER PUBLICATIONS

Ellingboe, et al., (Pyrimidinyloxy)acetic Acids and Pyrimidineacetic Acids as a Novel Class of Aldose Reductase Inhibitors, Journal of Medicinal Chemistry, 1990, vol. 33, pp. 2892-2899, American Chemical Society.

Aso, et al., "Discovery of pyrrolo[2,3-d]pyrimidin-4-ones as corticotropin-releasing factor 1 receptor agonists with a carbonyl-based hydrogen bonding acceptor", Bioorganic & Medicinal Chemistry Letters, 2011, pp. 2365-237, vol. 21, Elsevier Ltd.

Fortanet, et al., "Allosteric Inhibition of SHP2: Identification of a Potent, Selective, and Orally Efficacious Phosphatase Inhibitor", Journal of Medicinal Chemistry, Jun. 27, 2016, pp. 7773-7782, vol. 59, American Chemical Society.

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: biphosphorylated peptide derived from insulin
      receptor substrate-1 (IRS-1)
<220> FEATURE:
<221> NAME/KEY: MOD_RES
<222> LOCATION: (3)..(3)
<223> OTHER INFORMATION: PHOSPHORYLATED TYROSINE
<220> FEATURE:
<221> NAME/KEY: MISC_FEATURE
<222> LOCATION: (10)..(10)
<223> OTHER INFORMATION: dPEG8
<220> FEATURE:
<221> NAME/KEY: MOD_RES
<222> LOCATION: (14)..(14)
<223> OTHER INFORMATION: PHOSPHORYLATED TYROSINE
<220> FEATURE:
<221> NAME/KEY: MOD_RES
<222> LOCATION: (21)..(21)
<223> OTHER INFORMATION: AMIDATED LYSINE

<400> SEQUENCE: 1

Leu Asn Tyr Ile Asp Leu Asp Leu Val Xaa Leu Ser Thr Tyr Ala Ser
1               5                   10                  15

Ile Asn Phe Gln Lys
            20

1-PYRIDAZIN-/TRIAZIN-3-YL-PIPER (-AZINE)/IDINE/PYROLIDINE DERIVATIVES AND COMPOSITIONS THEREOF FOR INHIBITING THE ACTIVITY OF SHP2

CROSS-REFERENCE TO RELATED APPLICATIONS

This application is a 371 U.S. national phase application of international application number PCT/IB2015/050343 filed 16 Jan. 2015, which application claims the benefit of priority under 35 U.S.C. § 119(e) to U.S. Provisional Patent Application No. 61/928,738, filed 17 Jan. 2014. The disclosure of these applications are incorporated herein by reference in their entirety and for all purposes.

BACKGROUND

Field of the Invention

The present invention relates to compounds capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

Background of the Invention

The Src Homology-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present invention fulfill the need of small molecules to that inhibit the activity of SHP2.

SUMMARY OF THE INVENTION

In one aspect, the present invention provides compounds of Formula I:

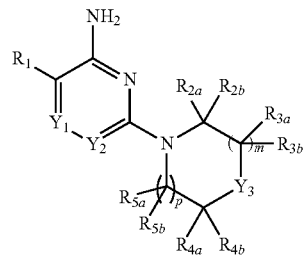

in which: m is selected from 0, 1 and 2; p is selected from 0 and 1; $Y_1$ is selected from CH and N; $Y_2$ is selected from $CR_6$ and N; $Y_3$ is selected from NH and $CR_7R_8$; $R_1$ is selected from $C_{6-10}$aryl, $C_{3-8}$cycloalkyl, $C_{3-8}$cycloalkenyl and a 5-9 member heteroaryl group containing from 1 to 4 heteroatoms selected from N, O and S; wherein said aryl or heteroaryl of $R_1$ is substituted with 1 to 5 $R_9$ groups independently selected from halo, amino, hydroxy, $N_3$, $C_{1-4}$alkyl, hydroxy-substituted-$C_{1-4}$alkyl, halo-substituted-$C_{1-4}$alkyl, amino-substituted-$C_{1-4}$alkyl, —C(O)O$R_{10}$ and —NHC(O)$R_{10}$; $R_{10}$ is selected from hydrogen, phenyl and naphthyl; wherein said phenyl of $R_{10}$ is unsubstituted or substituted with methoxy; $R_{2a}$ and $R_{2b}$ are independently selected from hydrogen, $C_{1-4}$alkyl, $C_{1-4}$alkoxy, amino, hydroxy, $C_{3-8}$cycloalkyl and $C_{1-4}$alkyl-amino; $R_{3a}$ and $R_{3b}$ are independently selected from hydrogen, halo, carbonyl, $C_{1-4}$alkyl, $C_{1-4}$alkoxy, amino, hydroxy, $C_{3-8}$cycloalkyl and $C_{1-4}$alkyl-amino; $R_{4a}$ and $R_{4b}$ are independently selected from hydrogen, halo, carbonyl, $C_{1-4}$alkyl, $C_{1-4}$alkoxy, amino, hydroxy, $C_{3-8}$cycloalkyl and $C_{1-4}$alkyl-amino; $R_{5a}$ and $R_{5b}$ are independently selected from hydrogen, carbonyl, $C_{1-4}$alkyl, $C_{1-4}$alkoxy, amino, hydroxy, $C_{3-8}$cycloalkyl and $C_{1-4}$alkyl-amino; wherein any two groups selected from $R_{2a}$, $R_{3a}$, $R_{4a}$ and $R_7$ can form a 5 to 6 member unsaturated, partially unsaturated ring or saturated ring optionally containing a ring nitrogen; $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$alkyl, —S(O)$_{1-2}$$R_{6a}$, —C(S)$R_{6a}$, —C(O)N$R_{6a}R_{6b}$, —C(NH)N$R_{6a}R_{6b}$ and —N$R_{6a}$C(O)$R_{6b}$; wherein $R_{6a}$ and $R_{6b}$ are independently selected from hydrogen and $C_{1-4}$alkyl; $R_7$ is selected from hydrogen, $C_{1-4}$alkyl, $C_{3-6}$cycloalkyl, $C_{6-10}$aryl and a 5-9 member heteroaryl group containing from 1 to 4 heteroatoms selected from N, O and S; $R_7$ and $R_{4a}$ together with the carbon atoms to which they are both attached can form a fused pyrrolidinyl or cyclopropyl group substituted with amino (such as example 19, infra); $R_8$ is selected from amino, amino-methyl and methyl-amino; or a pharmaceutically acceptable salt thereof.

In a second aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In a third aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof, in simultaneous or sequential combination with an anticancer therapeutic.

In a fifth aspect, the present invention provides the use of a compound of Formula I in the manufacture of a medicament for treating a disease in an animal in which SHP2 activity contributes to the pathology and/or symptomology of the disease.

In a sixth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, ten-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, cyclohexenyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60R, D61Y, V, N; Y62D; E69K; A72T, V; T73I; E76K, V, G, A, Q; E139D; G503A, R; Q506P (JMML); G60V; D61V; E69K; F71L; A72V; E76A (MDS); Y63C (CMML); Y62C; E69K; T507K (neuroblastoma); V46L; N58S; E76V (Lung cancer); R138Q (melanoma); E76G (colon cancer).

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis- (=Z—) or trans (=E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

For the following compounds, the NH2 group attached to the pyrazine ring is critical for potency. Analysis of the crystallographic structure shows the NH2 group in an intramolecular interaction with the backbone carbonyl group of SHP2 residue E250:

| Compound | SHP2 IC50 |
|---|---|
| 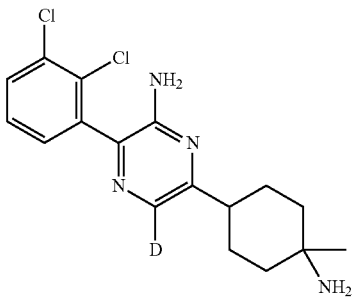 [SMILES: [2H]c1nc(-c2cccc(Cl)c2Cl)c(N)nc1C1CCC(C)(N)CC1] | 70 nM |
| (structure with Cl, Cl, NH2, pyrazine, piperidine-NH2) | 5.7 μM |

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. For example, compound can exist in a deuterated form as shown below:

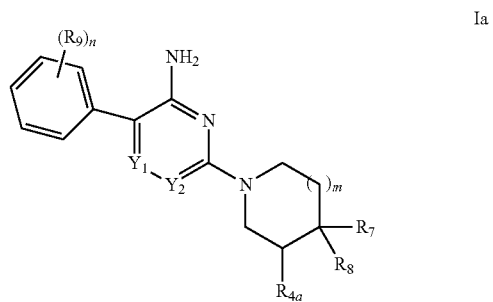

DESCRIPTION OF PREFERRED EMBODIMENTS

The present invention relates to compounds capable of inhibiting the activity of SHP2. In one aspect of the invention, with respect to compounds of Formula I, are compounds of Formula Ia:

Ia (structure showing pyrimidine with $(R_9)_n$ phenyl, $NH_2$, $Y_1$, $Y_2$, piperidine with $R_{4a}$, $R_7$, $R_8$)

in which: m is selected from 0 and 1; n is selected from 1, 2, 3, 4 and 5; $Y_1$ is selected from CH and N; $Y_2$ is selected from $CR_6$ and N; $R_{4a}$ is selected from hydrogen, methyl and hydroxy; $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$alkyl, —S(O)$_{1-2}$R$_{6a}$, —C(S)R$_{6a}$, —C(O)NR$_{6a}$R$_{6b}$, —C(NH)NR$_{6a}$R$_{6b}$ and —NR$_{6a}$C(O)R$_{6b}$; wherein R$_{6a}$ and R$_{6b}$ are independently selected from hydrogen and $C_{1-4}$alkyl; $R_7$ is selected from hydrogen, methyl, phenyl, pyrazinyl and pyridinyl; $R_7$ and $R_{4a}$ together with the carbon atoms to which they are both attached can form a cyclopropyl group substituted with amino; $R_8$ is selected from amino and methyl-amino; $R_9$ is selected from halo, amino, hydroxy, $N_3$, $C_{1-4}$alkyl, halo-substituted-$C_{1-4}$alkyl, $C_{1-4}$alkoxy, —C(O)OR$_{10}$ and —NHC(O)R$_{10}$; $R_{10}$ is selected from hydrogen, phenyl and naphthyl; wherein said phenyl of $R_{10}$ is unsubstituted or substituted with methoxy; or a pharmaceutically acceptable salt thereof.

In a further aspect of the invention are compounds, or the pharmaceutically acceptable salt thereof, selected from:

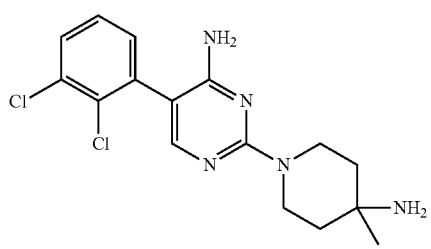
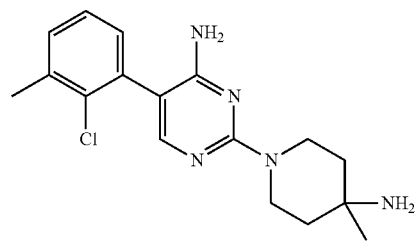 [SMILES: Cc1cccc(-c2cnc(N3CCC(C)(N)CC3)nc2N)c1Cl]
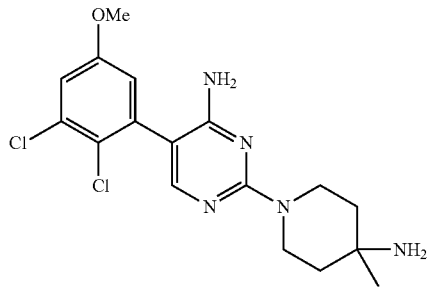 [SMILES: COc1cc(Cl)c(Cl)c(-c2cnc(N3CCC(C)(N)CC3)nc2N)c1]
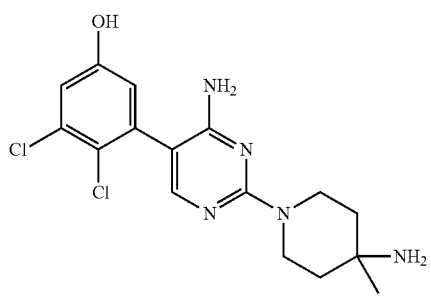
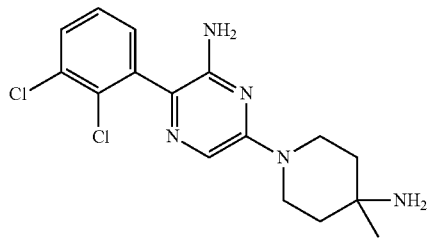
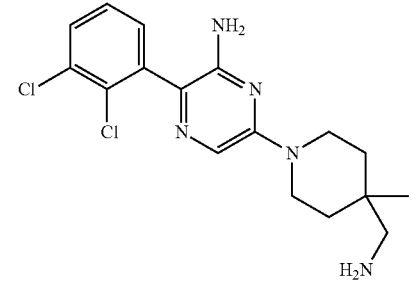 [SMILES: CC1(CN)CCN(c2cnc(-c3cccc(Cl)c3Cl)c(N)n2)CC1]
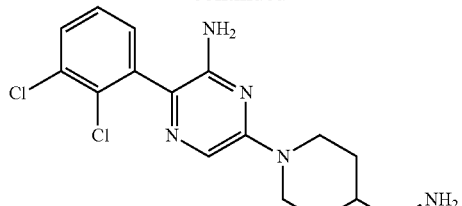
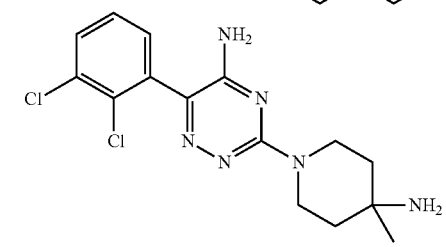
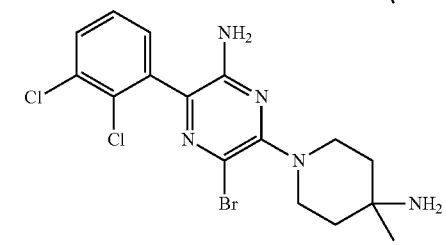
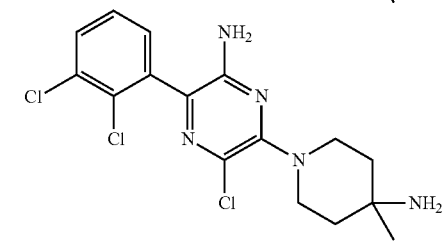
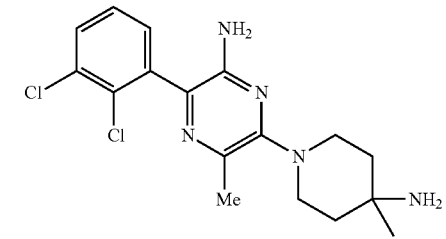
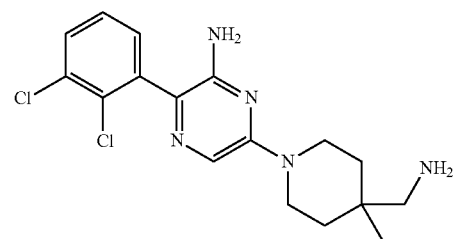
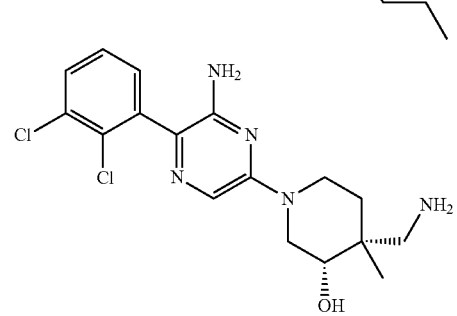

-continued

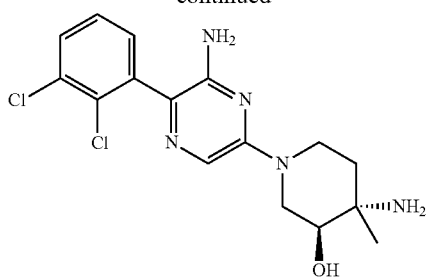
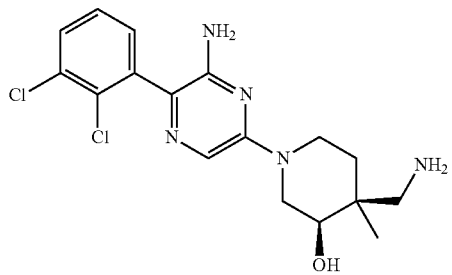
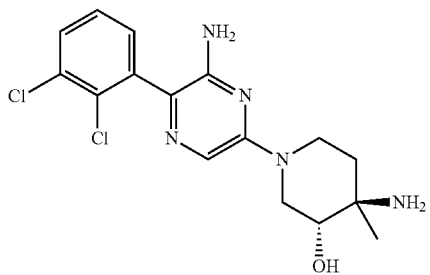
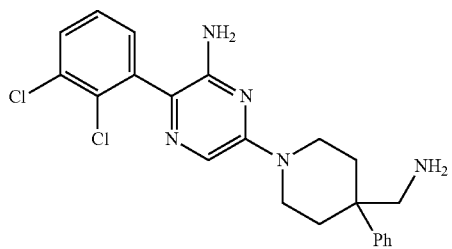 [SMILES: NCC1(c2ccccc2)CCN(c2cnc(-c3cccc(Cl)c3Cl)c(N)n2)CC1]
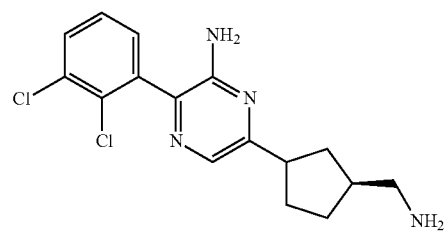
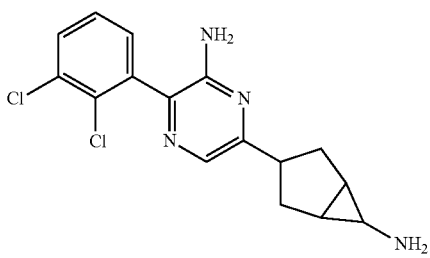

-continued

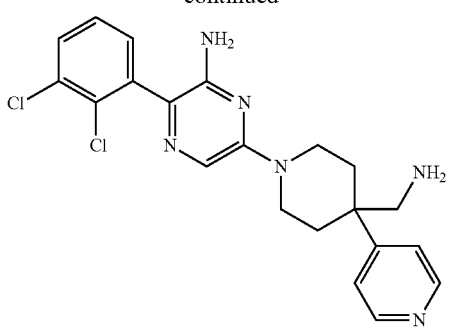
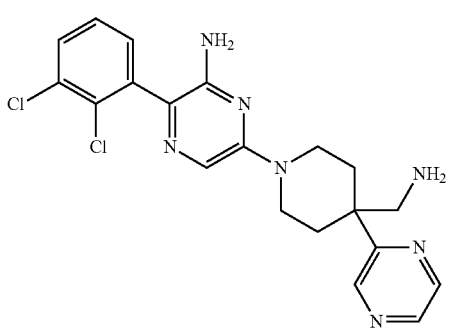

In another aspect of the invention are compounds of formula Ib:

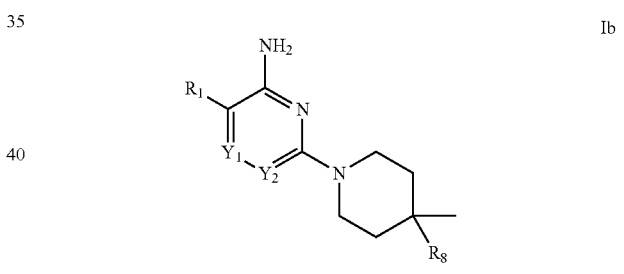

Ib in which: $Y_1$ is selected from CH and N; $Y_2$ is selected from $CR_6$ and N; $R_1$ is selected from thiophen-2-yl and 1H-indol-7-yl; wherein said thiophen-2-yl can be substituted with a group selected from methyl and chloro; $R_6$ is selected from hydrogen, halo and methyl; $R_8$ is selected from amino and methyl-amino; or a pharmaceutically acceptable salt thereof.

In a further aspect of the invention are compounds, or the pharmaceutically acceptable salt thereof, selected from:

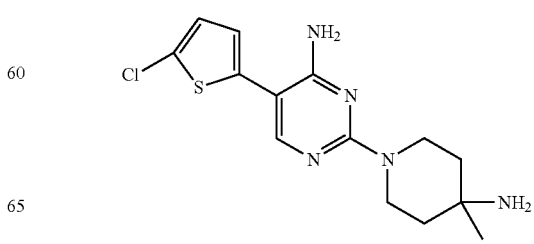

In another aspect of the invention are compounds of formula Ic:

Ic in which: n is selected from 1, 2, 3, 4 and 5; $Y_1$ is selected from CH and N; $Y_2$ is selected from $CR_6$ and N; $R_{3a}$ is selected from $C_{1-4}$alkyl, $C_{1-4}$alkoxy, amino, hydroxy, $C_{3-8}$cycloalkyl and $C_{1-4}$alkyl-amino; $R_{4a}$ is selected from hydrogen, $C_{1-4}$alkyl, $C_{1-4}$alkoxy, amino, hydroxy, $C_{3-8}$cycloalkyl and $C_{1-4}$alkyl-amino; $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$alkyl, —S(O)$_{1-2}$R$_{6a}$, —C(S)R$_{6a}$, —C(O)NR$_{6a}$R$_{6b}$, —C(NH)NR$_{6a}$R$_{6b}$ and —NR$_{6a}$C(O)R$_{6b}$; wherein $R_{6a}$ and $R_{6b}$ are independently selected from hydrogen and $C_{1-4}$alkyl; $R_{10}$ is selected from hydrogen, phenyl and naphthyl; wherein said phenyl of $R_{13}$ is unsubstituted or substituted with methoxy; or a pharmaceutically acceptable salt thereof.

In a further aspect of the invention are compounds, or the pharmaceutically acceptable salt thereof, selected from:

In another aspect of the invention are compounds, or the pharmaceutically acceptable salt thereof, selected from:

In another aspect of the invention are compounds, or the pharmaceutically acceptable salt thereof, selected from:

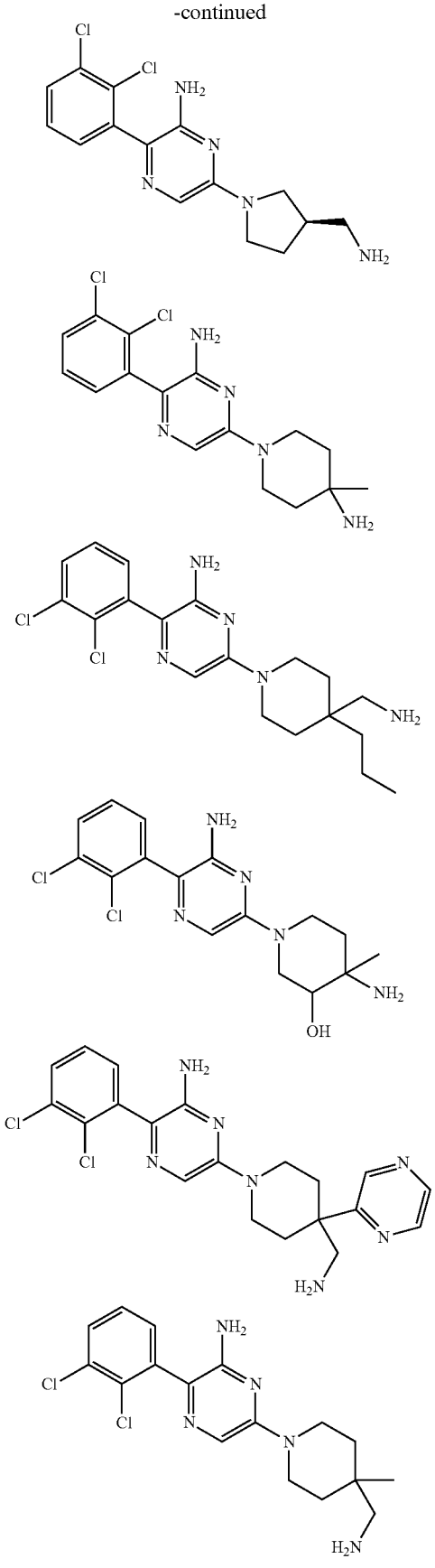

Pharmacology and Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS)—PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML)—Somatic mutations in PTPN11 (SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N-SH2 domain, resulting in SHP2 activity.

Acute Myeloid Leukemia—PTPN11 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations ($EGFR^{amp}$, $Her2^{amp}$, $FGFR^{amp}$, $Met^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastic Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary of the Invention.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemothereutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyimide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

A compound of formula (I) can also be used in combination with the following compounds:

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3); and LGX818.

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705A; and CH5424802.

BRAF inhibitors: Vemurafanib (PLX4032); and Dabrafenib.

FLT3 inhibitors—sunitinib malate (sold under the tradename Sutent® by Pfizer); and PKC412 (midostaurin).

MEK Inhibitors—trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxypurin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc);

Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl] benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®;

Biologic response modifiers: *bacillus* calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-$N^2$-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl) phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®);

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

A compound of formula (I) can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, can be prepared by proceeding as in the following Reaction Scheme I:

Reaction Scheme I:

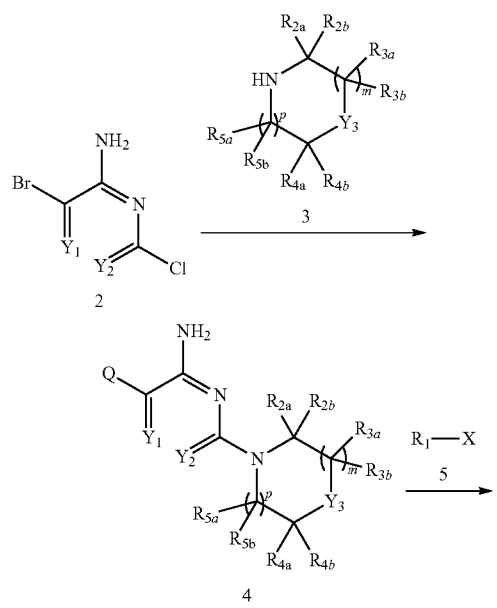

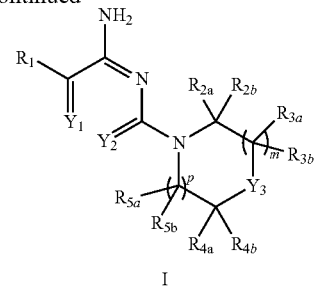

I m, p, $Y_1$, $Y_2$, $Y_3$, $R_1$, $R_{2a}$, $R_{2b}$, $R_{3a}$, $R_{3b}$, $R_{4a}$, $R_{4b}$, $R_{5a}$ and $R_{5b}$ are as defined for Formula I in the Summary of the Invention and Q is a halogen (like bromine) or a thiol, boronate or stannate which reacts with a halogen on compound 5 and X is a reactive group which reacts with Q (such as a boronate, stannane, alcohol, thiol, halogen, and the like). Compound 4 may be prepared by reacting compound 2 with compound 3 through a reaction under suitable acid or base conditions in the presence or absence of a transition metal under ambient temperature, or under thermal or microwave conditions. Alternatively, the halogen of compound 2 may be replaced by other halogens or suitable activating groups such as triflates, mesylates, tosylates, nonaflates, boronates, organostannanes, organosilyls, organozincs, lithium, magnesium, and the like.

A compound of formula I can be prepared by reacting compound 4 with a suitable coupling partner (e.g. compound 5) depending on X. For example, compound 5 is shown in reaction scheme I as a substituted phenyl group linked via X. Alternatively, compound 5 could be aryl-alcohol, aryl-thio, aryl-boronate, aryl-stannate, heteroaryl-alcohol, aryl-thiol, heteroaryl-thiol, aryl-boronate, aryl-stannane, olefin, or other aryl-metals or heteroaryl-metals, and the like. The coupling partners may also be substituted. This reaction may be conducted under suitable acid or base conditions, in the presence or absence of a transition metal such as palladium, under ambient temperature, or under thermal or microwave conditions. Other halogens or suitable activating groups (e.g., triflates, mesylates, tosylates, and nonaflates) may be used in place of Br for these transformations.

Alternatively, the coupling partners could be reversed and compound 2 may be derivatized to a stannane, boronate, organo-zinc, organo-lithium, organo-magnesium, organo-silicon, organo-cuprate and coupled with a suitable aryl-halide, heteroaryl-halide, olefin or suitable reactive functional group (e.g., triflates, mesylates, tosylates and nonaflates), and the like.

These reactions may be conducted in the order described or in reverse order, under a variety of solvents, temperatures, pressures, and under suitable atmospheres. The reactions may be conducted under acid, base, and or transition metal conditions.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e g, ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof. Some abbreviations used in the examples are as follows: acetic acid (AcOH); triethylamine (TEA); tetrahydrofuran (THF); aqueous (aq.); atmosphere (atm.); 2,2'-bis-diphenylphosphanyl-[1,1']binaphthalenyl (BINAP); 4-dimethylaminopyridine (DMAP); tert-butoxycarbonyl (Boc); 1,1-carbonyldiimidazole (CDI); di-tert-butyl dicarbonate (BOC$_2$O); benzotriazole-1-yl-oxy-tris-(dimethylamino)-phosphonium hexafluorophosphate (BOP); dichloromethane (DCM); diethyl ether (Et$_2$O); p-toluene sulfonic acid (PTSA); ethyl acetate (EtOAc); ethanol (EtOH); lithium bis(trimethylsilyl)amide (LHMDS); diisopropyl azodicarboxylate (DIAD); N,N-diisopropyl-ethylamine (DIEA or DIPEA); N,N-dimethylformamide (DMF); dimethyl sulfoxide (DMSO); diphenylphosphoryl azide (DPPA); hour(s) (h); 2-(1H-7-azabenzotriazol-1-yl)-1,1,3,3-tetramethyluronium hexafluorophosphate (HATU); High Performance Liquid Chromatography (HPLC); lithium aluminium hydride (LAH); liquid chromatography coupled with mass spectrometry (LCMS); lithium diisopropylamide (LDA); methanol (MeOH); milliliter(s) (mL); minute(s) (min); microwave (MW); n-butyllithium (n-BuLi); 1,1-bis(diphenylphosphino)-ferrocenedichloropalladium (II) (PdCl$_2$(dppf)); tris(dibenzylideneacetone)dipalladium (0) (Pd$_2$(dba)$_3$); dichlorobis(triphenylphosphine)palladium (II) (PdCl$_2$(PPh$_3$)$_2$); room temperature (RT); trifluoroacetic acid (TFA); tetrahydrofuran (THF); thin layer chromatography (TLC); retention time (t$_R$); & 4,5-bis(diphenylphosphino)-9,9-dimethylxanthene (Xantophos).

Intermediate 1

2-(2,3-dichloro-5-methoxyphenyl)-4,4,5,5-tetramethyl-1,3,2-dioxaborolane

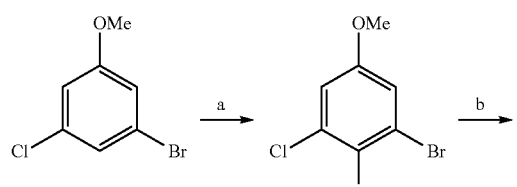

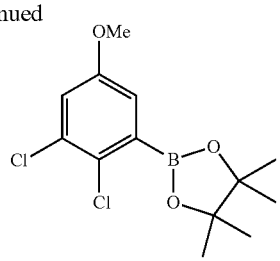

Step a: A solution of 1-bromo-3-chloro-5-methoxybenzene (835 mg, 3.77 mmol), and 1,3,5-trichloro-1,3,5-triazinane-2,4,6-trione (299 mg, 1.29 mmol) in DMF (18 mL) was stirred 16 h under N$_2$ and 50° C. After cooling to RT, the reaction mixture was diluted with aqueous NH$_4$Cl and extracted with Et$_2$O. The combined organic phases were dried over MgSO$_4$, filtered, concentrated, and the resulting residue was purified by silica chromatography (0 to 25% gradient of EtOAc/heptane) to 1-bromo-2,3-dichloro-5-methoxybenzene (720 mg, 2.81 mmol). $^1$H NMR (400 MHz, CHLOROFORM-d) δ ppm 7.14 (d, J=2.76 Hz, 1H), 7.01 (d, J=3.01 Hz, 1H), 3.81 (s, 3H).

Step b: A suspension of 1-bromo-2,3-dichloro-5-methoxybenzene (710 mg, 2.77 mmol), 4,4,4',4',5,5,5',5'-octamethyl-2,2'-bi(1,3,2-dioxaborolane) (775 mg, 3.05 mmol), potassium acetate (817 mg, 8.32 mmol), and PdCl$_2$(dppf) (101 mg, 0.139 mmol) in dioxane (5.5 mL) was stirred in a microwave reactor for 1 h at 100° C. to give the title compound as solution in dioxane that was used directly in Suzuki-Miyaura couplings.

Intermediate 2 tert-butyl (1-(4-amino-5-bromopyrimidin-2-yl)-4-methylpiperidin-4-yl)carbamate

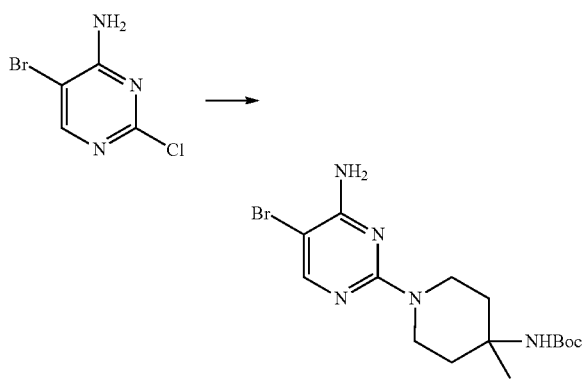

A solution of 5-bromo-2-chloropyrimidin-4-amine (650 mg, 3.12 mmol), tert-butyl (4-methylpiperidin-4-yl)carbamate (835 mg, 3.90 mmol), and 4-methylmorpholine (411 μL, 3.74 mmol) in NMP (6.25 mL) was stirred in a microwave reactor for 90 min at 130° C. The resulting residue was poured into water (100 mL) and was stirred at RT for 5 min. The solid formed was filtered off and dried under high vacuum for 16 h to give tert-butyl (1-(4-amino-5-bromopyrimidin-2-yl)-4-methylpiperidin-4-yl)carbamate (880 mg, 2.28 mmol). MS m/z 387.3 (M+H)$^+$.

Intermediate 3 tert-butyl (3-bromo-6-(4-((tert-butoxycarbonyl)amino)-4-methylpiperidin-1-yl)pyrazin-2-yl)(tert-butoxycarbonyl)carbamate

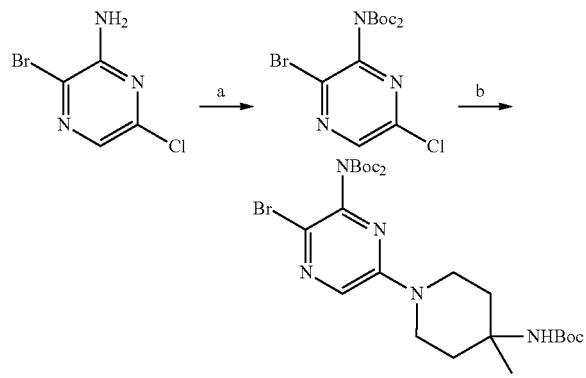

Step a: A solution of 3-bromo-6-chloropyrazin-2-amine (10.0 g, 48.0 mmol), DMAP (2.99 g, 24.47 mmol) and, di-tert-butyl dicarbonate (26.2 g, 120 mmol) in DCM (96 mL) was stirred 16 h at RT. The reaction mixture was diluted with brine and extracted with EtOAc. The combined organic phases were dried over MgSO$_4$, filtered, concentrated and the resulting residue was purified by silica chromatography (0 to 30% gradient of EtOAc/heptane) to give tert-butyl (3-bromo-6-chloropyrazin-2-yl)carbamate (18.77 g, 45.9 mmol). $^1$H NMR (400 MHz, CHLOROFORM-d) δ ppm 8.36 (s, 1H), 1.45 (s, 18H).

Step b: A solution of tert-butyl (3-bromo-6-chloropyrazin-2-yl)carbamate (11.9 g, 29.1 mmol), tert-butyl (4-methylpiperidin-4-yl)carbamate (12.48 g, 58.2 mmol), and 4-methylmorpholine (3.84 mL, 34.9 mmol) in NMP (58 mL) was stirred 16 h at 90° C. After cooling to RT, the reaction mixture was poured into H$_2$O (300 mL) and the solid formed was filtered off. This solid was further purified by silica chromatography (0 to 30% gradient of EtOAc/heptane (containing 0.25% v/v of Et$_3$N)) to give tert-butyl (3-bromo-6-(4-((tert-butoxycarbonyl)amino)-4-methylpiperidin-1-yl)pyrazin-2-yl)(tert-butoxycarbonyl)carbamate (80% purity). This compound was further purified by silica chromatography (0 to 7% gradient of EtOAc/DCM (containing 0.25% v/v of Et$_3$N)) to give tert-butyl (3-bromo-6-(4-((tert-butoxycarbonyl)amino)-4-methylpiperidin-1-yl)pyrazin-2-yl)(tert-butoxycarbonyl)carbamate (7.02 g, 11.97 mmol). MS m/z 586.5 (M+H)$^+$.

Intermediate 4 tert-butyl (1-(6-amino-5-bromopyrazin-2-yl)-4-methylpiperidin-4-yl)carbamate

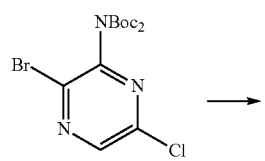

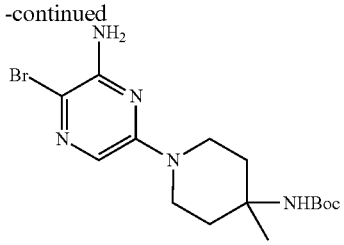

A solution of tert-butyl (3-bromo-6-chloropyrazin-2-yl)carbamate (8.184 g, 20.03 mmol), tert-butyl (4-methylpiperidin-4-yl)carbamate (8.58 g, 40.1 mmol), and 4-methylmorpholine (2.64 mL, 24.03 mmol) in NMP (50 mL) was stirred 16 h at 150° C. After cooling to RT, the reaction mixture was diluted with aqueous NaHCO$_3$ and extracted with Et$_2$O. The combined organic phases were dried over MgSO$_4$, filtered, concentrated, and the resulting residue was purified by silica chromatography (4 to 40% gradient of EtOAc/heptane) to give tert-butyl (1-(6-amino-5-bromopyrazin-2-yl)-4-methylpiperidin-4-yl)carbamate (1.629 g, 4.01 mmol). MS m/z 388.0 (M+H)$^+$.

Intermediate 5

3-bromo-6-((3S,5R)-3,5-dimethylpiperazin-1-yl)pyrazin-2-amine

A suspension of 3-bromo-6-chloropyrazin-2-amine (250 mg, 1.199 mmol) and (2S,6R)-2,6-dimethylpiperazine (151 mg, 1.319 mmol) in DIPEA (1.5 mL, 8.59 mmol) was stirred for 16 h at 130° C. After cooling to RT, the volatiles were removed under reduced pressure, the resulting solid was suspended in H$_2$O, filtered and the solid was further purified by HPLC (gradient elution 35-60% acetonitrile in water, 5 mM NH$_4$OH modifier) to give 3-bromo-6-((3S,5R)-3,5-dimethylpiperazin-1-yl)pyrazin-2-amine (40.0 mg, 0.140 mmol). MS m/z (M+H)$^+$287.0.

Intermediate 6

6-(4-amino-4-methylpiperidin-1-yl)-3-(2,3-dichlorophenyl)pyrazin-2-amine

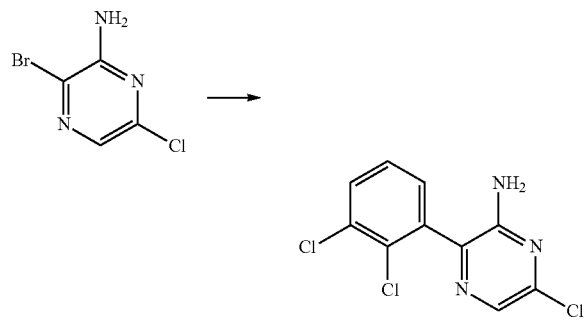

A suspension of 3-bromo-6-chloropyrazin-2-amine (1.2 g, 5.76 mmol), (2,3-dichlorphenyl)boronic acid (1.1 g, 5.76 mmol), potassium phosphate (3.67 g, 17.27 mmol), and PdCl$_2$(dppf).DCM adduct (235 mg, 0.288 mmol) in MeCN:H$_2$O (9:1, 15 mL, degassed) was stirred in a microwave reactor for 4 h at 120° C. After cooling to RT, the reaction was filtered through a pad of Celite followed by EtOAc (25 mL) wash. The combined filtrates were concentrated and the resulting residue was purified by silica chromatography (0 to 30% gradient of EtOAc/heptane) to give 6-(4-amino-4-methylpiperidin-1-yl)-3-(2,3-dichlorophenyl)pyrazin-2-amine (633 mg, 2.306 mmol). MS m/z 276.4 (M+H)$^+$.

Intermediate 7 tert-butyl (1-(5-amino-6-bromo-1,2,4-triazin-3-yl)-4-methylpiperidin-4-yl)carbamate

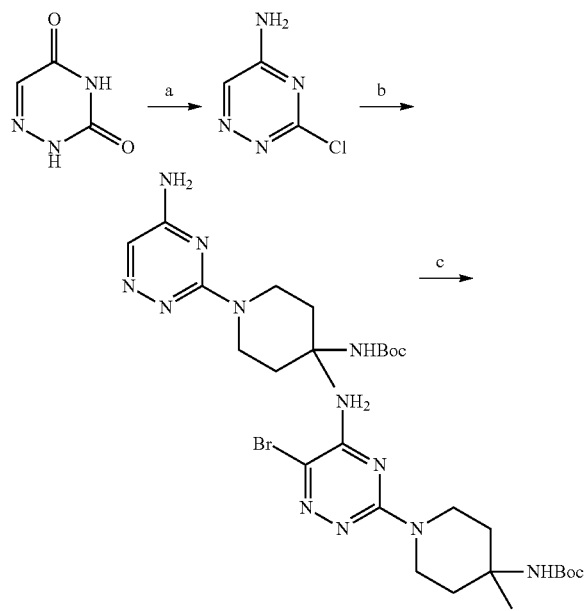

Step a: A solution of 6-azauracil (1.0 g, 8.84 mmol), POCl$_3$ (10 mL, 107 mmol), and N,N-dimethylaniline (2 mL, 1.784 mmol) was stirred in a microwave reactor for 25 min at 90° C. After cooling to RT, the reaction was poured into a beaker containing heptane (200 mL) stirred for 5 min at RT and the phases were separated. This procedure was repeated twice (200 mL of heptane each). The heptane phases were filtered through a pad of Celite and MgSO$_4$, the volatiles were removed under reduced pressure and the resulting residue was treated with NH$_3$ (7 N in MeOH, 5 mL in 10 mL of MeOH) precooled at 0° C. The mixture was stirred for 5 min at RT, then, the volatiles were removed to give 3-chloro-1,2,4-triazin-5-amine (200 mg, 17.3% yield). This compound was used in next step without further purification.

Step b: A solution of 3-chloro-1,2,4-triazin-5-amine (165 mg, 1.264 mmol), tert-butyl (4-methylpiperidin-4-yl)carbamate (271 mg, 1.264 mmol), and 4-methylmorpholine (208 µL, 1.896 mmol) in NMP (5 mL) was stirred in a microwave reactor for 3 h at 130° C. After cooling to RT, the resulting residue was purified by HPLC (gradient elution 15-40% acetonitrile in water, 5 mM NH$_4$OH modifier) to give tert-butyl (1-(5-amino-1,2,4-triazin-3-yl)-4-methylpiperidin-4-yl)carbamate (71.0 mg, 0.23 mmol). MS m/z 308.4 (M+H)$^+$.

Step c: A solution of tert-butyl (1-(5-amino-1,2,4-triazin-3-yl)-4-methylpiperidin-4-yl)carbamate (71 mg, 0.230 mmol) and NBS (41 mg, 0.230 mmol) in CHCl$_3$ (2 mL) was stirred 16 h at RT. The volatiles were removed under reduced pressure and the resulting residue was purified by silica chromatography (0 to 5% gradient of MeOH (containing 1% NH$_3$)/DCM) to give tert-butyl (1-(5-amino-6-bromo-1,2,4-triazin-3-yl)-4-methylpiperidin-4-yl)carbamate (87 mg, 0.23 mmol). MS m/z 387.3 (M+H)$^+$.

Intermediate 8 tert-butyl ((4-propylpiperidin-4-yl)methyl)carbamate

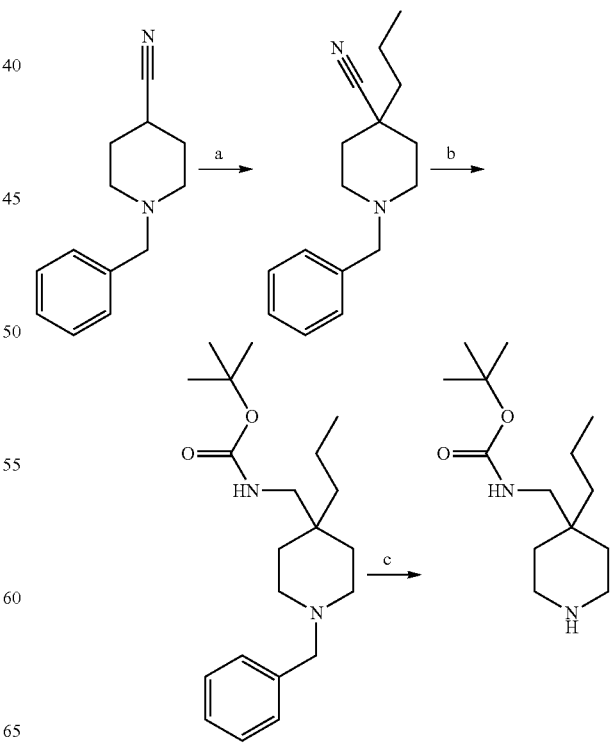

Step a: To a solution of N,N-diisopropylamine (14.0 mL, 97.5 mmol) in THF (100 mL) was added (at −78° C. and under $N_2$) n-butyllithium (1.6 M in hexane; 59.0 mL, 94.25 mmol) dropwise. The resulting mixture was stirred for 30 min at RT. 1-benzyl piperidine-4-carbonitrile (6.5 g, 32.5 mmol) in THF (50 mL) was added at −78° C. After stirring for 30 min at this temperature, n-propyl iodide (20.5 mL, 211.3 mmol) was added. The resulting mixture was stirred at −78° C. for 1 h. The mixture was quenched by addition of saturated aqueous ammonium chloride solution and it was extracted with EtOAc. The combined organic phases were washed with brine, dried over $Na_2SO_4$, filtered and concentrated to obtain 1-benzyl-4-propylpiperidine-4-carbonitrile (6.0 g, 24.8 mmol). This compound was used without further purification. MS m/z 243 $(M+H)^+$.

Step b: To a suspension of 1-benzyl-4-propylpiperidine-4-carbonitrile (1.0 g, 4.1 mmol) $Boc_2O$ (2.84 mL, 12.4 mmol), and $NiCl_2.6H_2O$ (0.195 g, 0.82 mmol) in MeOH (20 mL) was added at 0° C. sodium borohydride (1.0 g, 28.9 mmol) in portions. The resulting mixture was stirred for 12 h at RT. The volatiles were removed under reduced pressure. The resulting residue was dissolved in DCM, filtered through Celite and the volatiles were removed under reduced pressure. The resulting residue was purified by silica chromatography (0 to 15% gradient of EtOAc/heptane) to give tert-butyl ((1-benzyl-4-propylpiperidin-4-yl)methyl)carbamate (0.8 g, 2.3 mmol). MS m/z 347 $(M+H)^+$.

Step c: A suspension of tert-butyl ((1-benzyl-4-propylpiperidin-4-yl)methyl)carbamate (5.0 g, 14.4 mmol) and 10% Pd/C (2 g) in MeOH (100 mL) was vigorously stirred under $H_2$ (using a balloon) for 4 h at RT. The mixture was filtered through Celite followed by MeOH wash. The volatiles were removed under reduced pressure and the resulting residue was triturated from pentane to give tert-butyl ((4-propylpiperidin-4-yl)methyl)carbamate (2.7 g, 10.5 mmol) as a white powder. $^1$H NMR (400 MHz, DMSO-$d_6$) δ 6.68 (m, 1H), 2.87 (d, J=6.4 Hz, 2H), 2.69-2.53 (m, 4H), 1.38 (s, 9H), 1.18 (m, 8H), 0.84 (q, J=5.9 Hz, 3H). MS m/z 257 $(M+H)^+$.

Intermediate 9

2-((4-(pyridin-3-yl)piperidin-4-yl)methyl)isoindoline-1,3-dione

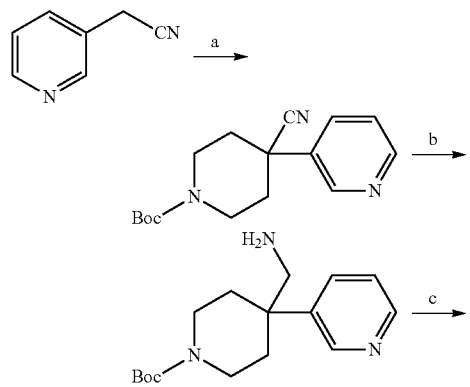

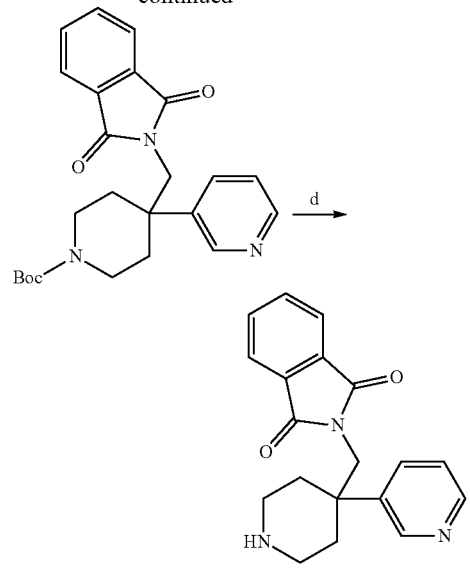

Step a: To a suspension of sodium hydride (60% in mineral oil, 1.487 g mg, 37.2 mmol) in DMF (25 mL) was added at 0° C. 2-(pyridin-3-yl)acetonitrile (1.537 g, 13.01 mmol) in DMF (5 mL) dropwise within 10 min. The resulting mixture was stirred 30 min at 0° C. Tert-butyl-bis (2-chloroethyl)carbamate (3.0 g, 12.39 mmol) in DMF (5 mL) was added at 0° C., the resulting mixture was stirred for 15 min at 0° C. and for 16 h at 75° C. After cooling to RT, the reaction mixture was diluted with $NaHCO_3$ aq. and extracted with $Et_2O$. The combined organic phases were dried over $MgSO_4$, filtered, concentrated and the resulting residue was purified by silica chromatography (10 to 80% gradient of EtOAc/heptane) to give tert-butyl 4-cyano-4-(pyridin-3-yl)piperidine-1-carboxylate (2.58 g, 8.98 mmol). $^1$H NMR (400 MHz, CHLOROFORM-d) δ ppm 8.69 (d, J=2.02 Hz, 1H), 8.55 (dd, J=4.80, 1.52 Hz, 1H), 7.68-7.81 (m, 1H), 7.30 (ddd, J=8.08, 4.80, 0.76 Hz, 1H), 4.25 (br. s., 2H), 3.15 (br. s., 2H), 2.06 (d, J=11.87 Hz, 2H), 1.81-1.98 (m, 2H), 1.42 (s, 9H).

Step b: To a solution of tert-butyl 4-cyano-4-(pyridin-3-yl)piperidine-1-carboxylate (1.0 g, 3.48 mmol) in MeOH (30 mL) was added at RT, $CoCl_2.6H_2O$ (828 mg, 2.38 mmol) and sodium borohydride (658 mg, 17.40 mmol). The resulting mixture was stirred for 1 h at RT. The volatiles were removed under reduced pressure and the resulting residue was purified by silica chromatography (0 to 15% gradient of MeOH/DCM) to give tert-butyl 4-(aminomethyl)-4-(pyridin-3-yl)piperidine-1-carboxylate (683 mg, 2.344 mmol). MS m/z 292.2 $(M+H)^+$.

Step c: A suspension of tert-butyl 4-(aminomethyl)-4-(pyridin-3-yl)piperidine-1-carboxylate (683 mg, 2.344 mmol), phthalic anhydride (434 mg, 2.93 mmol), activated molecular sieves (3 angstroms, 500 mg), and DIPEA (1.23 mL, 7.03 mmol) in toluene (12 mL) was stirred for 16 h at 105° C. After cooling to RT, the mixture was filtered through a pad of Celite followed by EtOAc (10 mL) wash. The volatiles were removed under reduced pressure and the resulting residue was purified by silica chromatography (0 to 10% gradient of MeOH/DCM) to give tert-butyl 4-((1,3-dioxoisoindolin-2-yl)methyl)-4-(pyridin-3-yl)piperidine-1-carboxylate (640 mg, 1.518 mmol). MS m/z 422.3 $(M+H)^+$.

Step d: A solution of tert-butyl 4-((1,3-dioxoisoindolin-2-yl)methyl)-4-(pyridin-3-yl)piperidine-1-carboxylate (640 mg, 1.518 mmol) and HCl (4M in dioxane, 1.9 mL, 7.59 mmol) in dioxane (20 mL) was stirred for 16 h at RT. The volatiles were removed under reduced pressure to give the HCl salt of the title compound (543 mg, 1.518 mmol). MS m/z 322.2 (M+H)+.

Intermediate 10 tert-butyl ((4-(pyrazin-2-yl)piperidin-4-yl)methyl) carbamate

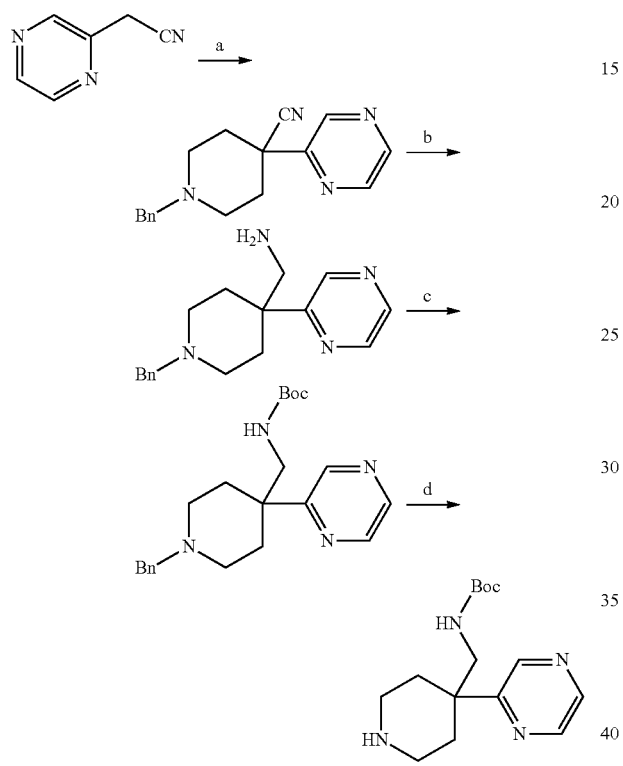

Step a: To a suspension of sodium hydride (60% in mineral oil, 1.90 g, 47.7 mmol) in DMF (30 mL) was added at 0° C. 2-(pyrazin-2-yl)acetonitrile (1.90 g, 15.90 mmol) in DMF (5 mL) dropwise within 10 min. The resulting mixture was stirred 30 min at 0° C. N-benzyl-2-chloro-N-(2-chloroethyl)ethanamine (4.7 g, 17.5 mmol) in DMF (5 mL) was added at 0° C., the resulting mixture was stirred for 15 min at 0° C. and for 16 h at 90° C. After cooling to RT, the reaction mixture was diluted with NaHCO₃ aq. and extracted with EtOAc (3×25 mL). The combined organic phases were dried over Na₂SO₄, filtered, concentrated, and the resulting residue was purified by trituration with hexane to give 1-benzyl-4-(pyrazin-2-yl)piperidine-4-carbonitrile (1.60 g, 5.76 mmol).

Step b: To a solution of 1-benzyl-4-(pyrazin-2-yl)piperidine-4-carbonitrile (1.50 g, 5.39 mmol) in NH₃ (7 N in MeOH, 50 mL) was added at RT Raney nickel (750 mg). The resulting suspension was vigorously stirred under H₂ (60 psi) at RT until the starting material disappeared (16 h). The reaction mixture was filtered through a pad of Celite followed by MeOH (50 mL) wash. The volatiles were removed under reduced pressure to give (1-benzyl-4-(pyrazin-2-yl)piperidin-4-yl)methanamine (1.20 g, 4.25 mmol) which was used in next step without further purification. MS m/z 319 (M+H)+.

Step c: A solution of (1-benzyl-4-(pyrazin-2-yl)piperidin-4-yl)methanamine (1.20 g, 4.25 mmol), Et₃N (1.17 mL, 8.51 mmol), and Boc₂O (1.95 mL, 8.51 mmol) in DCM (50 mL) was stirred for 2 h at RT. The reaction was diluted with H₂O and it was extracted with DCM (3×25 mL). The combined organic phases were washed with brine, dried over Na₂SO₄, filtered and the volatiles were removed under reduced pressure. The resulting residue was purified by silica chromatography (0 to 100% gradient of EtOAc/heptane) to give tert-butyl ((1-benzyl-4-(pyrazin-2-yl)piperidin-4-yl)methyl) carbamate (1.30 g, 3.40 mmol). MS m/z 383 (M+H)+.

Step d: A suspension of tert-butyl ((1-benzyl-4-(pyrazin-2-yl)piperidin-4-yl)methyl)carbamate (1.50 g, 3.93 mmol) and Pd(OH)₂ (20% on carbon, 600 mg, 50% moisture) in MeOH (20 mL) was vigorously stirred under H₂ (50 psi) for 3 h at RT. The reaction mixture was filtered through a pad of Celite followed by MeOH (50 mL) wash. The volatiles were removed under reduced pressure and to give tert-butyl ((4-(pyrazin-2-yl)piperidin-4-yl)methyl)carbamate (1.10 g, 3.76 mmol) which was used without further purification. MS m/z 283 (M+H)+.

The following intermediates were made using the above procedure or modifications to the above procedure using the corresponding commercial available heteroaromatic nitriles.

TABLE 1

| Intermediate | Structure |
| --- | --- |
| 11 | ![structure] |
| 12 | ![structure] |

Intermediate 13

Racemic trans-4-amino-4-methylpiperidin-3-ol

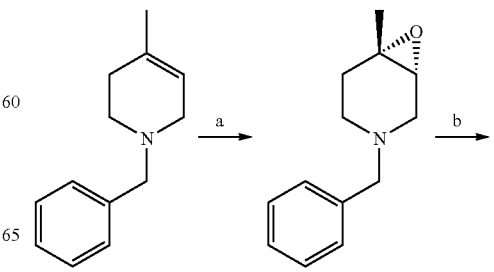

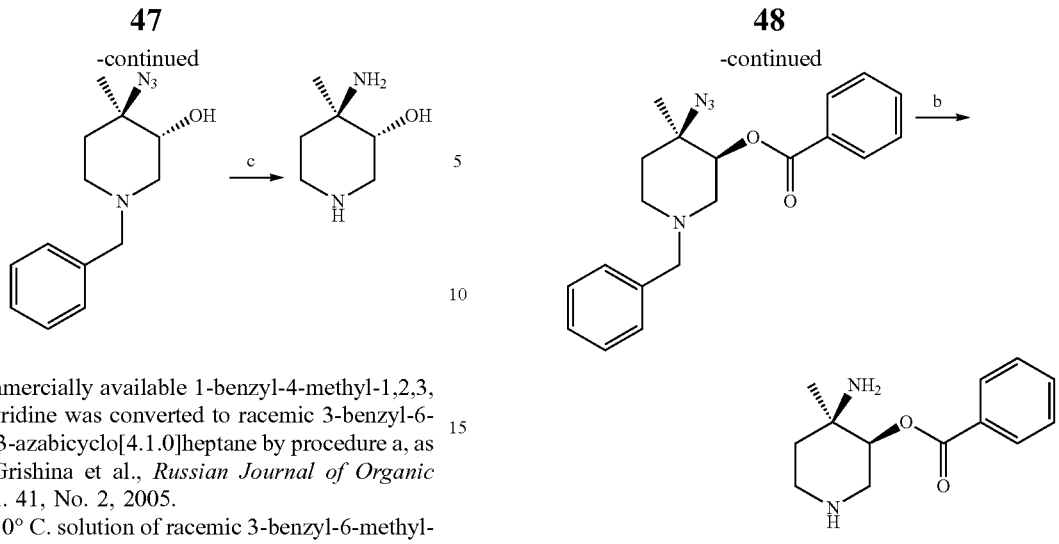

Step a: Commercially available 1-benzyl-4-methyl-1,2,3,6-tetrahydropyridine was converted to racemic 3-benzyl-6-methyl-7-oxa-3-azabicyclo[4.1.0]heptane by procedure a, as described in Grishina et al., *Russian Journal of Organic Chemistry*, vol. 41, No. 2, 2005.

Step b: To a 0° C. solution of racemic 3-benzyl-6-methyl-7-oxa-3-azabicyclo[4.1.0]heptane (4.5 g, 22.153 mmol) in water (45 mL) and acetic acid (22 mL) was added sodium azide (7.2 g, 110.766 mmol). The reaction was warmed to RT and stirred for 16 h. The reaction was quenched by addition of saturated aq sodium bicarbonate (60 mL). The mixture was extracted with DCM (3×200 mL) and EtOAc (2×150 mL) and the combined organic extracts were washed with brine, dried over $Na_2SO_4$, filtered, and concentrated. The crude product was purified by silica gel chromatography (25 to 30% gradient of EtOAc/heptane) to give racemic trans-4-azido-1-benzyl-4-methylpiperidin-3-ol (3.3 g, 16.23 mmol). $^1$H NMR (400 MHz, $CDCl_3$): δ ppm 7.34-7.24 (m, 5H), 3.53 (s, 2H), 3.35 (s, 1H), 2.70-2.57 (m, 3H), 3.32-2.26 (m, 1H), 1.89-1.81 (m, 1H), 1.59-1.55 (m, 1H), 1.37 (s, 3H). MS m/z 247.4 $(M+H)^+$.

Step c: To a solution of racemic trans-4-azido-1-benzyl-4-methylpiperidin-3-ol (474 mg, 1.926 mmol) in MeOH was added a catalytic amount of Pd/C. The solution was degassed and backfilled with $H_2$ 2×. The reaction was stirred for 1 h, LCMS indicated that SM was consumed. The reaction was filtered through Celite/sand (MeOH). This resulted in the isolation of 444 mg (yellow oil/semisolid). $^1$H NMR indicated incomplete reduction (aromatic peaks detected), so the above procedure was repeated. The reaction was filtered through Celite/sand and concentrated. $^1$H NMR confirmed the absence of aromatic peaks. 247 mg of a viscous oil resulted which was used with no further purification.

Intermediate 14

Racemic cis-4-azido-4-methylpiperidin-3-yl benzoate

Step a: To a solution of racemic trans-4-azido-1-benzyl-4-methylpiperidin-3-ol (500 mg, 2.03 mmol) in DCM (20 mL) was added benzoic acid (273 mg, 2.233 mmol), di-tert-butylazodicarboxylate (514 mg, 2.233 mmol), and triphenylphosphine (586 mg, 2.233 mmol). The reaction was stirred for 16 h at RT. The reaction was diluted with DCM (100 mL) and washed with saturated aq sodium bicarbonate (100 mL). The organic layer was dried over $MgSO_4$, filtered, and concentrated and the resulting residue was purified by silica chromatography (0 to 20% gradient of EtOAc/heptane) to give racemic cis-4-azido-1-benzyl-4-methylpiperidin-3-yl benzoate (92 mg, 0.263 mmol) as a yellow oil which solidified to an off-white crystalline solid. $^1$H NMR (DMSO-$d_6$) δ ppm 8.37 (d, J=9.0 Hz, 2H), 8.19 (d, J=8.9 Hz, 2H), 7.31-7.18 (m, 6H), 4.44-4.32 (m, 2H), 4.08 (d, J=13.3 Hz, 1H), 3.60 (d, J=13.3 Hz, 1H), 3.0 (dd, J=4.4, 6.4 Hz, 1H), 2.79-2.73 (m, 1H), 2.49-2.42 (m, 1H), 1.92-1.85 (m, 2H), 1.49 (s, 3H). MS m/z 351.1 $(M+H)^+$.

Step b: To a solution of racemic cis-4-azido-1-benzyl-4-methylpiperidin-3-yl benzoate (90 mg, 0.257 mmol) in MeOH (50 mL) was added 10% Pd/C (50 mg). The reaction was degassed and backfilled 3× with $H_2$ (balloon). The reaction was stirred for 16 h. The crude reaction mixture was filtered through Celite (MeOH) and the solution collected was concentrated, to give racemic cis-4-azido-4-methylpiperidin-3-yl 4-nitrobenzoate (48 mg, 0.184 mmol). The crude material was used without further purification. MS m/z 235.2 (M+H).

Intermediate 15

Racemic tert-butyl trans-((3-hydroxy-4-methylpiperidin-4-yl)methyl)carbamate

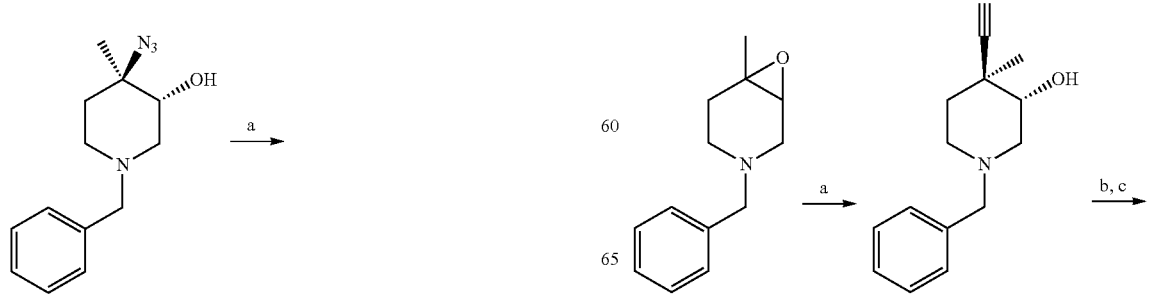

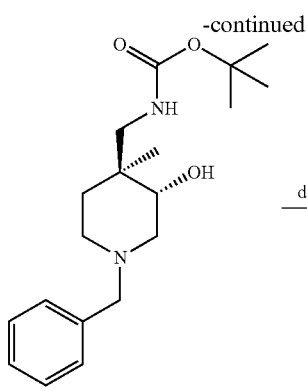

Step a: A solution of lithium hydride (0.118 g, 14.8 mmol) in THF (20 mL) was added at 0° C. acetone cyanohydrin (1.4 mL, 14.8 mmol). The resulting reaction mixture was stirred for 2 h at RT. The volatiles were removed under reduced pressure to give a white solid. To a solution of this solid in THF (60 mL) was added at RT 3-benzyl-6-methyl-7-oxa-3-azabicyclo[4.1.0]heptane (2.0 g, 9.85 mmol) dropwise. After complete addition, the solution was stirred for 14 h under reflux. After cooling to RT, water (10 mL) was added and the resulting mixture was extracted with EtOAc (3×100 mL). The combined organic phases were washed with brine, dried over Na$_2$SO$_4$, filtered and concentrated. The resulting residue was purified by silica chromatography (0 to 20% gradient of EtOAc/heptane) to obtain racemic trans-1-benzyl-3-hydroxy-4-methylpiperidine-4-carbonitrile (0.70 g, 3.0 mmol). $^1$H NMR (400 MHz, DMSO-d$_6$) δ 7.36-7.22 (m, 5H), 5.25 (d, J=6.0 Hz, 1H), 3.70-3.67 (m, 1H), 3.49 (dd, J=13.2, 10.4 Hz, 2H), 2.37 (m, 3H), 1.88-1.74 (m, 2H), 1.25 (s, 3H). MS m/z 231.2 (M+H)$^+$.

Step b: A suspension of racemic trans-1-benzyl-3-hydroxy-4-methyl piperidine-4-carbonitrile (1.3 g, 5.6 mmol) and Raney nickel (50% in water, 600 mg) in ammonia (7 N in EtOH; 80 mL) was vigorously stirred under hydrogen (balloon) for 6 h at RT. The mixture was filtered through Celite under N$_2$ and washed with MeOH. The volatiles were removed under reduced pressure to give trans-4-(aminomethyl)-1-benzyl-4-methylpiperidin-3-ol (1.6 g, 4.79 mmol). This compound was used in next step without further purification. MS m/z 235.2 (M+H)$^+$.

Step c: A solution of trans-4-(aminomethyl)-1-benzyl-4-methylpiperidin-3-ol (1.6 g, 4.79 mmol), Boc$_2$O (2.84 mL, 12.4 mmol), and NaHCO$_3$ (0.935 g, 11.1 mmol) in CHCl$_3$ (70 mL) was stirred for 14 h at RT. The mixture was diluted with DCM and washed with ice water, brine, dried over Na$_2$SO$_4$, filtered and concentrated. The resulting residue was purified by silica chromatography (0 to 5% gradient of MeOH/DCM) to give racemic tert-butyl trans-(1-benzyl-3-hydroxy-4-methylpiperidin-4-yl)methyl)carbamate (1.6 g, 4.79 mmol). MS m/z 335.3 (M+H)$^+$.

Step d: A suspension of racemic tert-butyl trans-((1-benzyl-3-hydroxy-4-methylpiperidin-4-yl)methyl)carbamate (1.1 g, 3.3 mmol) and Pd(OH)$_2$ (20% on charcoal; 0.250 g) in MeOH (60 mL) was vigorously stirred under hydrogen atmosphere (balloon) for 6 h at RT. The resulting mixture was filtered through Celite and washed with MeOH. Concentrated, then triturated from hexane (10 mL) and diethyl ether (2 mL) to give racemic tert-butyl trans-((3-hydroxy-4-methylpiperidin-4-yl)methyl)carbamate (0.70 g, 2.87 mmol) as a white powder. $^1$H NMR (400 MHz, METHANOL-d$_4$) δ 3.42 (dd, J=9.9, 4.4 Hz, 1H), 3.12 (d, J=13.9 Hz, 1H), 2.94-2.84 (m, 2H), 2.82-2.68 (m, 2H), 2.62 (dd, J=12.5, 10.0 Hz, 1H), 1.44 (s, 9H), 1.41-1.30 (m, 2H), 0.91 (s, 3H). MS m/z 245.1 (M+H)$^+$.

Intermediate 16

Racemic tert-butyl cis-((3-hydroxy-4-methylpiperidin-4-yl)methyl)carbamate

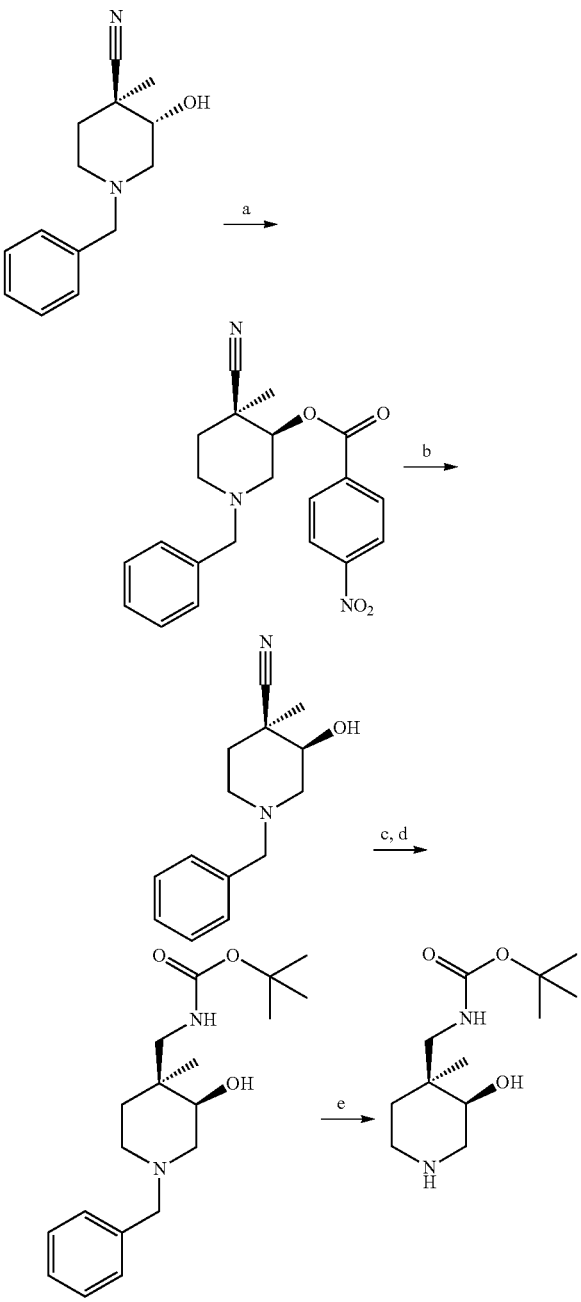

Step a: A solution of racemic trans-1-benzyl-3-hydroxy-4-methyl piperidine-4-carbonitrile (2.0 g, 8.70 mmol), triphenylphosphine (3.41 g, 13.0 mmol), and diisopropylazodicarboxylate (2.63 g, 13.0 mmol) in THF (30 mL) was stirred for 10 min at 0° C. 4-Nitrobenzoic acid (2.18 g, 13.0 mmol) was added portionwise and the resulting mixture was stirred for 16 h at RT. The mixture was diluted with water and extracted with EtOAc. The combined organic phases were washed with brine, dried over Na$_2$SO$_4$, filtered and concentrated. The resulting residue was triturated with MeOH to give racemic cis-1-benzyl-4-cyano-4-methylpiperidin-3-yl 4-nitrobenzoate (1.5 g, 3.96 mmol). MS m/z 380 (M+H)$^+$. This material was used without further purification.

Step b: A solution of racemic cis-1-benzyl-4-cyano-4-methylpiperidin-3-yl 4-nitrobenzoate (1.5 g, 3.96 mmol) and potassium carbonate (1.07 g, 7.92 mmol) in MeOH (20 mL) was vigorously stirred for 10 min at 0° C. and for 1 h at RT. The volatiles were removed under reduced pressure. The resulting residue was diluted with water and extracted with EtOAc (3×). The combined organic phases were washed with brine, dried over Na$_2$SO$_4$, filtered and concentrated. The resulting residue was purified by silica chromatography (0 to 15% gradient of EtOAc/heptane) to give racemic cis-1-benzyl-3-hydroxy-4-methylpiperidine-4-carbonitrile (0.8 g, 3.5 mmol). $^1$H NMR (400 MHz, CDCl$_3$) δ 7.36-7.26 (m, 5H), 3.99 (d, J=12.4 Hz, 1H), 3.67 (d, J=12.8, 1H), 3.60-3.51 (m, 2H), 3.11-3.07 (m, 2H), 2.76-2.69 (m, 2H), 2.24 (dd, J=12.8, 6.0 Hz, 1H), 1.87-1.80 (m, 1H), 1.54 (s, 3H). MS m/z 231 (M+H)$^+$.

Step c: A suspension of cis-1-benzyl-3-hydroxy-4-methylpiperidine-4-carbonitrile (800 mg, 3.5 mmol) and Raney nickel (50% in water, 700 mg) in ammonia (7 N in EtOH; 20 mL) was vigorously stirred under hydrogen (balloon) for 16 h at RT. The mixture was filtered through Celite under N$_2$ and washed with MeOH. The volatiles were removed under reduced pressure to give racemic cis-4-(aminomethyl)-1-benzyl-4-methylpiperidin-3-ol (700 mg, 3.0 mmol). This compound was used in next step without further purification. MS m/z 235.2 (M+H)$^+$.

Step d: A solution of cis-4-(aminomethyl)-1-benzyl-4-methylpiperidin-3-ol (700 mg, 3.0 mmol), Boc$_2$O (1.1 mL, 2.99 mmol), and Et$_3$N (860 μL, 5.98 mmol) in DCM (10 mL) was stirred for 2 h at RT. The mixture was diluted with DCM and washed with ice water, brine, dried over Na$_2$SO$_4$, filtered and concentrated. The resulting residue was purified by silica chromatography (0 to 50% gradient of EtOAc/heptane) to give racemic tert-butyl cis-(1-benzyl-3-hydroxy-4-methylpiperidin-4-yl)methyl)carbamate (700 mg, 2.10 mmol). This compound was used in next step without further purification. MS m/z 335 (M+H)$^+$.

Step e: A suspension of racemic tert-butyl cis-(1-benzyl-3-hydroxy-4-methylpiperidin-4-yl)methyl)carbamate (700 mg, 2.1 mmol) and Pd/C (10% on charcoal; 300 mg) in MeOH (20 mL) was vigorously stirred under hydrogen atmosphere (balloon) for 5 h at RT. The resulting mixture was filtered through Celite and washed with MeOH and concentrated. The resulting residue was purified by silica chromatography (0 to 10% gradient of MeOH/DCM) to give racemic tert-butyl cis-((3-hydroxy-4-methylpiperidin-4-yl)methyl)carbamate (200 mg, 0.8 mmol) as a white powder. $^1$H NMR (400 MHz, METHANOL-d$_4$) δ 3.73-3.67 (m, 1H), 3.59 (dd, J=11.1, 7.7 Hz, 1H), 3.15-2.99 (m, 4H), 1.90 (m, 1H), 1.62 (m, 1H), 1.47 (m, 1H), 1.44 (s, 9H), 0.96 (s, 3H). MS m/z 245 (M+H)$^+$.

Example 1

2-(4-amino-4-methylpiperidin-1-yl)-5-(2,3-dichlorophenyl)pyrimidin-4-amine

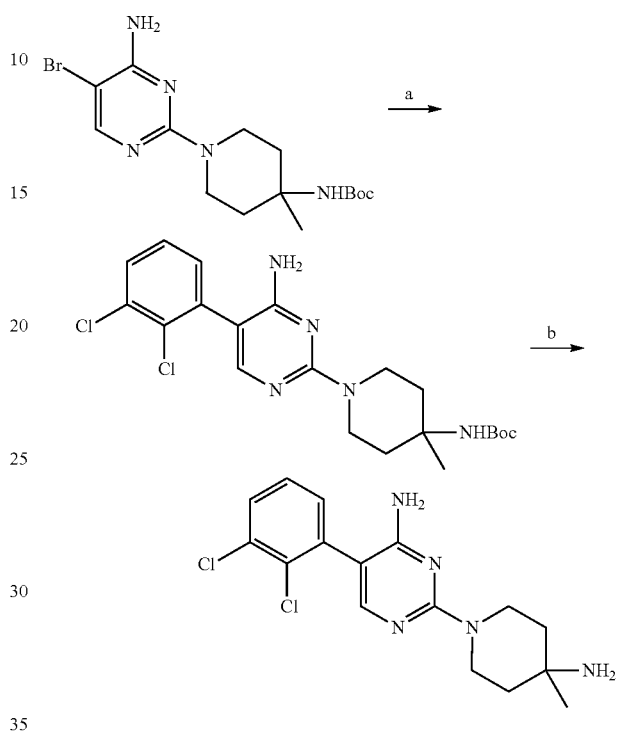

Step a: A suspension of tert-butyl (1-(4-amino-5-bromopyrimidin-2-yl)-4-methylpiperidin-4-yl)carbamate (966 mg, 2.50 mmol), (2,3-dichlorphenyl)boronic acid (596 mg, 3.13 mmol), potassium phosphate (1.59 g, 7.50 mmol), and PdCl$_2$(dppf).DCM adduct (204 mg, 0.25 mmol) in MeCN:H$_2$O (9:1, 10 mL, degassed) was stirred in a microwave reactor for 3 h at 110° C. After cooling to RT, the reaction was filtered through a pad of Celite followed by EtOAc (50 mL) wash. The combined filtrates were concentrated and the resulting residue was purified by silica chromatography (0 to 5% gradient of MeOH/DCM) to give tert-butyl (1-(4-amino-5-(2,3-dichlorophenyl)pyrimidin-2-yl)-4-methylpiperidin-4-yl)carbamate (1.07 g, 2.37 mmol). MS m/z 452.4 (M+H)$^+$.

Step b: To a solution of tert-butyl (1-(4-amino-5-(2,3-dichlorophenyl)pyrimidin-2-yl)-4-methylpiperidin-4-yl)carbamate (2.14 g, 4.73 mmol) in DCM (50 mL), was added TFA (31.7 mL). After stirring at 0° C. until no starting material remained (30 min, monitored by LCMS), the volatiles were removed under reduced pressure and the resulting residue was purified by HPLC (gradient elution 10-30% acetonitrile in water, 0.1% TFA modifier), to give the title compound (657 mg, 1.69 mmol; HCl salt). $^1$H NMR (400 MHz, METHANOL-d$_4$) δ ppm 7.49-7.63 (m, 2H), 7.34 (t, J=7.71 Hz, 1H), 7.26 (d, J=7.33 Hz, 1H), 4.18 (d, J=12.13 Hz, 2H), 3.38-3.61 (m, 2H), 1.88 (br. s., 4H), 1.45 (s, 3H). HRMS calcd for C$_{16}$H$_{20}$Cl$_2$N$_5$ (M+H)$^+$ 352.1096, found 352.1086. IC$_{50}$ is 0.258 μM.

The following compounds were made using the above procedure or modifications to the above procedure using the corresponding boronic acid.

TABLE 2

| Example | Compound | Characterization | IC$_{50}$ (μM) |
|---|---|---|---|
| 2 | | $^1$H NMR (400 MHz, METHANOL-d$_4$) δ ppm 7.50 (s, 1 H), 7.19-7.25 (m, 1 H), 7.12-7.19 (m, 1 H), 6.98-7.04 (m, 1 H), 3.88 (ddd, J = 13.64, 6.32, 4.55 Hz, 2 H), 3.48-3.56 (m, 2 H), 2.33 (s, 3 H), 1.47-1.54 (m, 4 H), 1.16 (s, 3 H). HRMS calcd for C$_{17}$H$_{22}$ClN$_5$ (M + H)$^+$ 332.1642, found 332.1645. | 0.858 |
| 3 | | as TFA salt. $^1$H NMR (400 MHz, DMSO-d$_6$) δ ppm 7.92 (br. s., 4 H), 7.88 (s, 1 H), 7.16 (d, J = 3.76 Hz, 1 H), 6.99 (d, J = 3.76 Hz, 1 H), 4.14-4.24 (m, 2 H), (piperidine methylene hidden by H$_2$O peak, 2 H), 1.68 (br. s., 4 H), 1.36 (s, 3 H). HRMS calcd for C$_{14}$H$_{18}$ClN$_5$S (M + H)$^+$ 324.1050, found 324.1045 | 0.950 |
| 4 | | as TFA salt. $^1$H NMR (400 MHz, DMSO-d$_6$) δ ppm 7.85-8.00 (m, 4 H), 7.83 (s, 1 H), 6.94 (br. s., 1 H), 6.84 (br. s., 1 H), 4.11-4.23 (m, 2 H), (piperidine methylene hidden by H$_2$O peak, 2 H), 2.46 (s, 3 H), 1.69 (br. s., 4 H), 1.37 (s, 3 H). HRMS calcd for C$_{15}$H$_{21}$N$_5$S (M + H)$^+$ 304.1596, found 304.1591 | 0.974 |
| 5 | | as TFA salt. $^1$H NMR (400 MHz, METHANOL-d$_4$) δ ppm 7.70 (s, 1 H), 7.27 (d, J = 3.03 Hz, 1 H), 6.96 (d, J = 2.78 Hz, 1 H), 4.27 (d, J = 13.64 Hz, 2 H), 3.86 (s, 3 H), 3.48-3.69 (m, 2 H), 1.98 (d, J = 5.05 Hz, 4 H), 1.55 (s, 3 H). HRMS calcd for C$_{17}$H$_{22}$Cl$_2$N$_5$O (M + H)$^+$ 382.1201, found 382.1256 | 2.859 |

Example 6

3-(4-amino-2-(4-amino-4-methylpiperidin-1-yl)pyrimidin-5-yl)-4,5-dichlorophenol

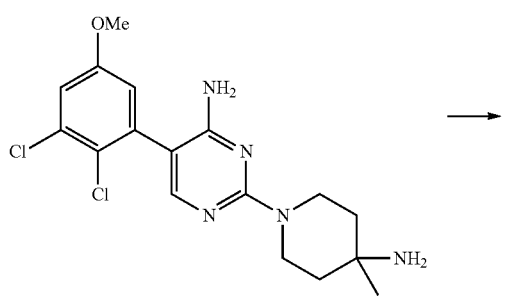

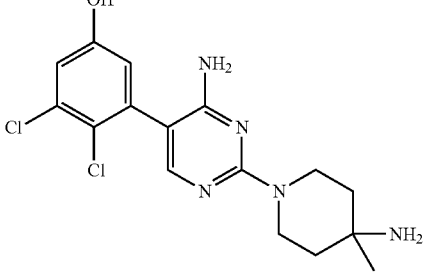

To a solution 2-(4-amino-4-methylpiperidin-1-yl)-5-(2,3-dichloro-5-methoxyphenyl)pyrimidin-4-amine (77 mg, 0.155 mmol) in DCM (5 mL) was added at −78° C. and under N$_2$, BBr$_3$ (1 M in DCM, 465 μL, 0.465 mmol). After stirring 16 h at RT, the volatiles were removed under reduced pressure and the resulting residue was purified by HPLC (gradient elution 10-30% acetonitrile in water, 5 mM NH$_4$OH modifier) to give the title compound (29.2 mg, 0.079 mmol). $^1$H NMR (400 MHz, METHANOL-d$_4$) δ ppm 7.51 (s, 1H), 6.83 (d, J=3.01 Hz, 1H), 6.53 (d, J=2.76 Hz, 1H), 3.84-4.02 (m, 2H), 3.40-3.62 (m, 2H), 1.40-1.63 (m, 4H), 1.19 (s, 3H). HRMS calcd for $C_{16}H_{20}Cl_2N_5O$ (M+H)$^+$ 368.1104, found 368.1086. IC$_{50}$ is 0.225 µM.

Example 7

6-(4-amino-4-methylpiperidin-1-yl)-3-(2,3-dichlorophenyl)pyrazin-2-amine

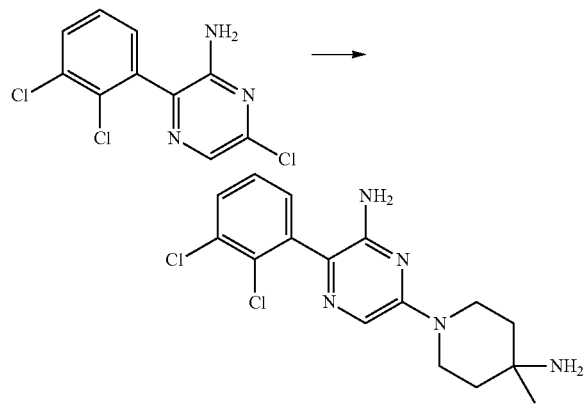

A solution of 6-(4-amino-4-methylpiperidin-1-yl)-3-(2,3-dichlorophenyl)pyrazin-2-amine (950 mg, 3.46 mmol), tert-butyl (4-methylpiperidin-4-yl)carbamate (1.48 g, 6.92 mmol) and, N-methylmorphpoline (761 µL, 6.92 mmol) in NMP (9 mL) was stirred in a microwave reactor for 2 h at 250° C. Note that under these reaction conditions, the Boc protecting group was removed. After cooling to RT, the reaction was purified by HPLC (gradient elution 15-40% acetonitrile in water, 0.1% TFA modifier) to give the title compound (750 mg, 01.885 mmol, HCl salt). $^1$H NMR (400 MHz, METHANOL-d$_4$) δ ppm 7.81 (dd, J=6.69, 2.91 Hz, 1H), 7.62 (s, 1H), 7.45-7.59 (m, 2H), 4.25 (br. s., 2H), 3.44-3.61 (m, 2H), 1.81-2.04 (m, 4H), 1.55 (s, 3H). HRMS calcd for $C_{16}H_{20}Cl_2N$ (M+H)$^+$ 352.1096, found 352.1099. IC$_{50}$ is 0.071 µM.

The following compounds were made using the above procedure or modifications to the above procedure using the corresponding amine. Although in most cases the Boc protecting group was removed under the reaction conditions, HCl or TFA was used when necessary.

TABLE 3

| Example | Compound | Characterization | IC$_{50}$ (µM) |
|---|---|---|---|
| 8 | (structure) | $^1$H NMR (400 MHz, METHANOL-d$_4$) δ ppm 7.70-7.68 (m, 1 H), 7.49-7.41 (m, 3 H), 4.01 (dt, J$_1$ = 13.7, J$_2$ = 4.3, 4.3 Hz, 2 H), 3.48-3.41 (m, 2 H), 2.91 (s, 2 H), 1.66-1.55 (m, 4 H), 1.19 (s, 3 H). HRMS calcd for $C_{17}H_{22}Cl_2N_5$ (M + H)$^+$ 366.1252, found 366.1240. | 0.076 |
| 9 | (structure) | $^1$H NMR (400 MHz, DMSO-d$_6$) δ ppm 7.62 (dd, J = 8.08, 1.52 Hz, 1 H), 7.48 (s, 1 H), 7.41-7.37 (m, 1 H), 7.32-7.29 (m, 1 H), 5.63 (br. S., 2 H), 4.31 (d, J = 12.5 Hz, 2 H), 2.86-2.67 (m, 4 H), 2.44 (d, J = 6.3, 2 H), 1.78-1.68 (m, 3 H), 1.13-1.03 (m, 2 H). HRMS calcd for $C_{16}H_{20}Cl_2N_5$ (M + H)$^+$ 352.1096, found 352.1087. | 0.358 |
| 10 | (structure) | $^1$H NMR (400 MHz, METHANOL-d$_4$) δ ppm 7.69-7.66 (m, 1 H), 7.47-7.37 (m, 3 H), 4.04 (dt, J$_1$ = 13.6, J$_2$ = 4.9, 4.9 Hz, 1 H), 3.95-3.90 (m, 1 H), 3.79-3.75 (m, 1 H), 3.72-3.66 (m, 1 H), 3.47-3.32 (overlapping with methanol, m, 3 H), 3.09-3.04 (m, 1 H), 2.69-2.63 (m, 1 H), 2.50-2.45 (m, 1 H), 2.25-2.11 (m, 3 H), 1.97-1.88 (m, 2 H). HRMS calcd for $C_{17}H_{20}Cl_2N_5$ (M + H)$^+$ 364.1096, found 364.1083. | 0.908 |

TABLE 3-continued

| Example | Compound | Characterization | IC$_{50}$ (μM) |
|---|---|---|---|
| 11 | 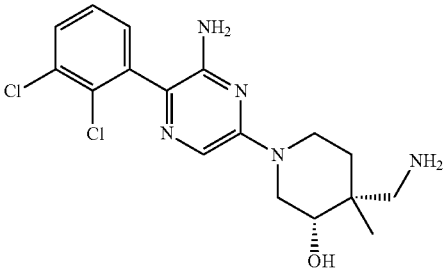 | Chiral SFC purification performed as follows; column: AD-H 21 x 250 mm, flow rate: 75 g per minute, mobile phase: 40% MeOH and 10 mM NH$_4$OH in CO$_2$, detection: 354 nm UV to obtain single enantiomer R$_t$ (P1) = 1.9 min, R$_t$ (P2) = 3.2 min. $^1$H NMR (400 MHz, DMSO-d$_6$) δ ppm 7.60 (dd, J = 7.96, 1.64 Hz, 1 H), 7.35-7.41 (m, 1 H), 7.30 (dd, J = 7.58, 1.77 Hz, 1 H), 7.22 (s, 1 H), 5.49 (s, 2 H), 3.71-3.80 (m, 2 H), 3.37-3.52 (m, 3 H), 2.32 (s, 2 H), 1.76-1.93 (m, 2 H), 1.04-1.11 (m, 3 H). HRMS calcd for C$_{17}$H$_{22}$Cl$_2$N$_5$O (M + H)$^+$ 382.1201, found 382.1220. | P1 = 0.038 P2 = 0.164 |
| 12 | 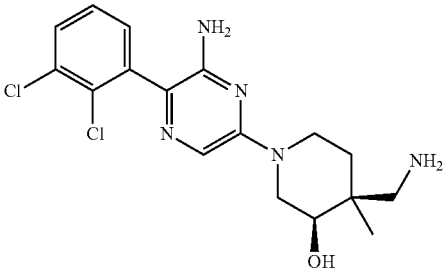 | $^1$H NMR (400 MHz, METHANOL-d$_4$) d 7.80 (dd, J = 2.27, 7.33 Hz, 1 H), 7.48-7.62 (m, 7 H), 7.37-7.46 (m, 1 H), 4.22 (br. s., 2 H), 3.37 (m, 2 H), 3.22 (s, 2 H), 2.54 (d, J = 14.15 Hz, 2 H), 1.99 (ddd, J = 3.66, 10.74, 14.15 Hz, 2 H). HRMS calcd for C$_{22}$H$_{24}$Cl$_2$N$_5$ (M + H)$^+$ 428.1409, found 428.1385. | 0.065 |
| 13 | 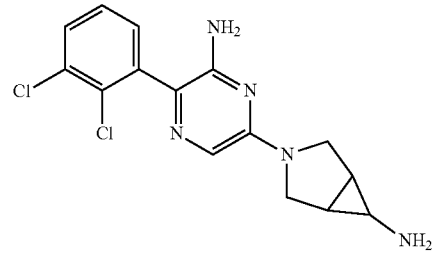 [SMILES: Nc1nc(N2CC3C(N)C3C2)cnc1-c1cccc(Cl)c1Cl] | $^1$H NMR (400 MHz, METHANOL-d$_4$) δ ppm 7.80 (dd, J = 2.01, 7.53 Hz, 1 H), 7.46-7.57 (m, 2 H), 7.29 (s, 1 H), 3.97 (d, J = 11.04 Hz, 2 H), 3.65-3.75 (m, 2 H), 2.55 (s, 1 H), 2.26 (br. s., 2 H). HRMS calcd for C$_{15}$H$_{16}$Cl$_2$N$_5$ (M + H)$^+$ 336.0782, found 336.0808. | 0.065 |
| 14 | 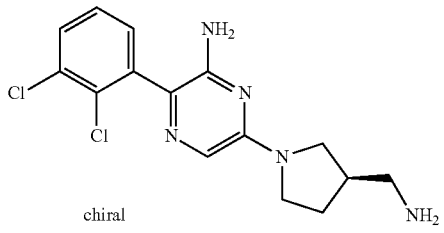 [SMILES: NC[C@H]1CCN(c2cnc(-c3cccc(Cl)c3Cl)c(N)n2)C1] chiral | $^1$H NMR (400 MHz, METHANOL-d$_4$) δ ppm 7.80 (dd, J = 2.38, 7.15 Hz, 1 H), 7.48-7.56 (m, 2 H), 7.28 (s, 1 H), 3.83-3.93 (m, 1 H), 3.77 (d, J = 7.03 Hz, 1 H), 3.55-3.65 (m, 1 H), 3.35-3.40 (m, 1 H), 3.06-3.21 (m, 2 H), 2.72 (td, J = 7.53, 15.06 Hz, 1 H), 2.32-2.42 (m, 1 H), 1.93 (qd, J = 8.45, 12.55 Hz, 1 H). HRMS calcd for C$_{15}$H$_{18}$Cl$_2$N$_5$ (M + H)$^+$ 338.0939, found 338.0938. | 0.068 |
| 15 | 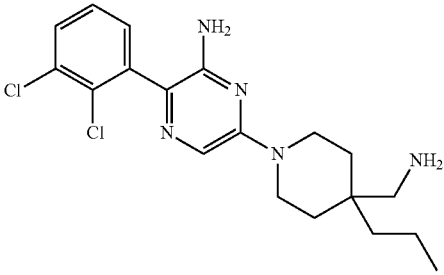 [SMILES: CCCC1(CN)CCN(c2cnc(-c3cccc(Cl)c3Cl)c(N)n2)CC1] | $^1$H NMR (400 MHz, DMSO-d$_6$) δ 7.61 (dd, J = 8.0, 1.6 Hz, 1 H), 7.46 (s, 1 H), 7.39 (t, J = 7.8 Hz, 1 H), 7.30 (dd, J = 7.7, 1.7 Hz, 1 H), 5.58 (s, 2 H), 3.55 (m, 2 H), 3.44 (m, 2 H), 3.32 (m, 2 H), 1.45 (m, 2 H), 1.40-1.28 (m, 4 H), 1.27-1.16 (m, 3 H), 0.89 (t, J = 7.0 Hz, 3 H). HRMS calcd for C$_{19}$H$_{26}$Cl$_2$N$_5$ (M + H)$^+$ 394.1565, found 394.1547. | 0.075 |

TABLE 3-continued

| Example | Compound | Characterization | IC$_{50}$ (μM) |
|---|---|---|---|
| 16 | 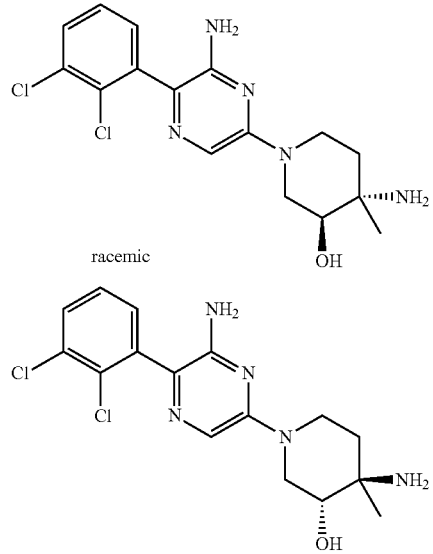 [SMILES: C[C@]1(N)CCN(c2cnc(-c3cccc(Cl)c3Cl)c(N)n2)C[C@@H]1O ; C[C@@]1(N)CCN(c2cnc(-c3cccc(Cl)c3Cl)c(N)n2)C[C@H]1O]<br>racemic | TFA salt. $^1$H NMR (400 MHz, DMSO-d$_6$) δ ppm 7.66 (dd, J = 1.6, 7.9 Hz, 1 H), 7.51 (s, 1 H), 7.43 (t, J = 7.8 Hz, 1 H), 7.36 (dd, J = 1.6, 7.8 Hz, 1 H), 4.45-4.31 (m, 2 H), 3.70 (dd, J = 5.0, 10.8 Hz, 1 H), 3.16-3.09 (m, 1 H), 2.93 (dd, J = 13.1, 13.1 Hz, 1 H), 1.97-1.91 (m, 1 H), 1.89-1.81 (m, 1 H), 1.45 (s, 3 H). HRMS calcd for C$_{16}$H$_{20}$N$_5$OCl$_2$ (M + H)$^+$ 368.1045, found 368.1049. | 0.093 |
| 17 | 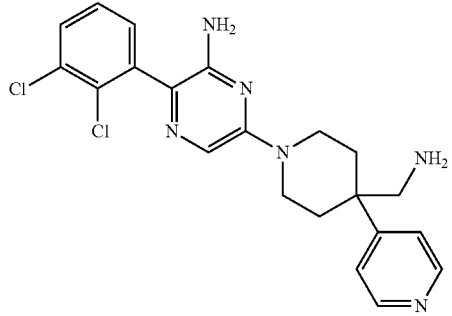 [SMILES: NCC1(c2ccncc2)CCN(c2cnc(-c3cccc(Cl)c3Cl)c(N)n2)CC1] | $^1$H NMR (400 MHz, METHANOL-d$_4$) δ ppm 8.97 (d, J = 7.1 Hz, 2 H), 8.35 (d, J = 7.1 Hz, 2 H), 7.78 (dd, J = 2.4, 7.2 Hz, 1 H), 7.58 (s, 1 H), 7.55-7.45 (m, 2 H), 4.16 (d, J = 13.6 Hz, 2 H), 3.55-3.41 (m, 4 H), 2.56 (d, J = 15.2 Hz, 2 H), 2.21 (ddd, J = 3.7, 9.8, 14.1 Hz, 2 H). HRMS calcd for C$_{21}$H$_{23}$Cl$_2$N$_6$ (M + H)$^+$ 429.1361, found 429.1338. | 0.102 |
| 18 | 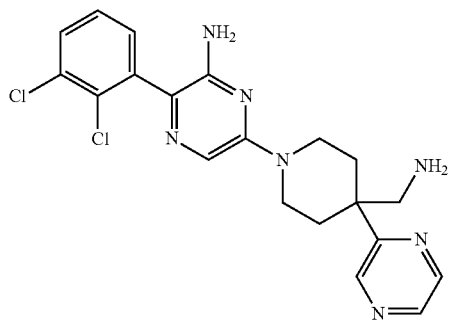 [SMILES: NCC1(c2cnccn2)CCN(c2cnc(-c3cccc(Cl)c3Cl)c(N)n2)CC1] | $^1$H NMR (400 MHz, METHANOL-d$_4$) δ ppm 8.94 (d, J = 1.3 Hz, 1 H), 8.77 (dd, J = 1.5, 2.5 Hz, 1 H), 8.65 (d, J = 2.3 Hz, 1 H), 7.81 (dd, J = 3.0, 6.6 Hz, 1 H), 7.59 (s, 1 H), 7.54 (d, J = 2.3 Hz, 1 H), 7.52 (s, 1 H), 4.22-4.09 (m, 2 H), 3.53-3.41 (m, 4 H), 2.71-2.62 (m, 2 H), 2.04 (ddd, J = 3.8, 9.7, 13.8 Hz, 2 H). HRMS calcd for C$_{20}$H$_{22}$Cl$_2$N$_7$ (M + H)$^+$ 430.1314, found 430.1325. | 0.093 |
| 19 | 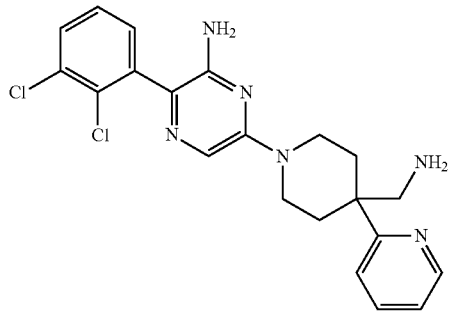 [SMILES: NCC1(c2ccccn2)CCN(c2cnc(-c3cccc(Cl)c3Cl)c(N)n2)CC1] | $^1$H NMR (400 MHz, METHANOL-d$_4$) δ ppm 8.80 (dd, J = 5.15, 0.88 Hz, 1 H) 8.22 (t, J = 7.78 Hz, 1 H) 7.91 (d, J = 8.28 Hz, 1 H) 7.82 (dd, J = 6.53, 3.01 Hz, 1 H) 7.66 (dd, J = 7.53, 5.27 Hz, 1 H) 7.60 (s, 1 H) 7.50-7.58 (m, 2 H) 4.13 (br. s., 2 H) 3.53 (dd, J = 13.18, 9.66 Hz, 2 H) 3.45 (s, 2 H) 2.62 (d, J = 15.06 Hz, 2 H) 2.01-2.18 (m, 2 H). HRMS calcd for C$_{21}$H$_{23}$Cl$_2$N$_6$ (M + H)$^+$ 429.1361, found 429.1357. | 0.110 |

TABLE 3-continued

| Example | Compound | Characterization | IC$_{50}$ (μM) |
|---|---|---|---|
| 20 | (structure) | $^1$H NMR (400 MHz, METHANOL-d$_4$) δ ppm 7.64 (dd, J = 8.03, 1.51 Hz, 1 H) 7.42 (t, J = 7.91 Hz, 1 H) 7.32 (dd, J = 7.65, 1.63 Hz, 1 H) 7.16 (s, 1 H) 5.12 (dd, J = 6.40, 3.64 Hz, 1 H) 4.23 (t, J = 8.16 Hz, 1 H) 3.77-3.87 (m, 2 H) 3.74 (d, J = 12.30 Hz, 1 H) 3.48 (dd, J = 7.15, 2.89 Hz, 1 H) 3.35-3.41 (m, 1 H) 3.23 (dd, J = 12.42, 3.64 Hz, 1 H). HRMS calcd for C$_{15}$H$_{16}$Cl$_2$N$_5$ (M + H)$^+$ 336.0783, found 336.0780. | 0.404 |
| 21 | (structure) | $^1$H NMR (400 MHz, METHANOL-d$_4$) δ ppm 7.80 (dd, J = 7.20, 2.40 Hz, 1 H) 7.48-7.57 (m, 2 H) 7.33 (s, 1 H) 3.77-3.89 (m, 2 H) 3.60-3.75 (m, 4 H) 3.29 (overlapping with methanol, d, 4 H). HRMS calcd for C$_{16}$H$_{18}$Cl$_2$N$_5$ (M + H)$^+$ 350.0939, found 350.0913. | 0.102 |

Example 22

6-(4-amino-4-methylpiperidin-1-yl)-5-bromo-3-(2,3-dichlorophenyl)pyrazin-2-amine

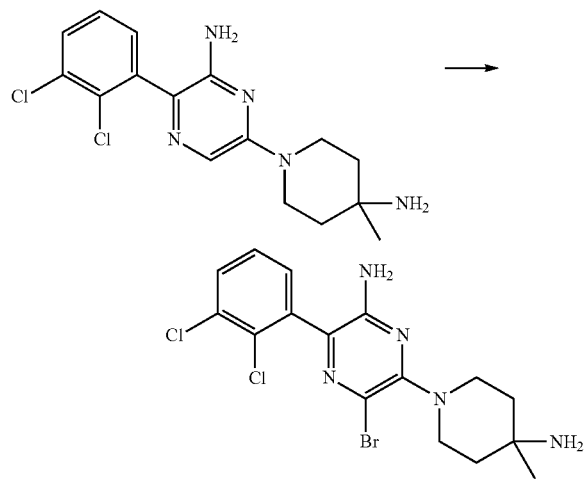

Example 23

6-(4-amino-4-methylpiperidin-1-yl)-5-chloro-3-(2,3-dichlorophenyl)pyrazin-2-amine

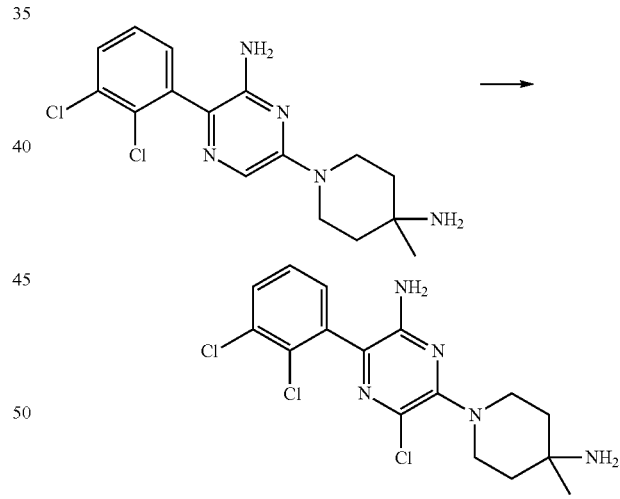

To a solution of 6-(4-amino-4-methylpiperidin-1-yl)-3-(2,3-dichlorophenyl)pyrazin-2-amine (275 mg, 0.590 mmol) in CH$_3$Cl (7 mL) was added at 0° C. and under N$_2$, Br$_2$ (32 μL, 0.619 mmol). After stirring for 2 h at 0° C., the volatiles were removed under reduced pressure and the resulting residue was purified by HPLC (gradient elution 35-60% acetonitrile in water, 5 mM NH$_4$OH modifier) to give the title compound (128.8 mg, 0.298 mmol). $^1$H NMR (400 MHz, METHANOL-d$_4$) δ ppm 7.63 (dd, J=7.96, 1.64 Hz, 1H), 7.42 (t, J=7.83 Hz, 1H), 7.36 (dd, J=7.58, 1.77 Hz, 1H), 3.52-3.62 (m, 2H), 3.35-3.40 (m, 2H), 1.76 (t, J=5.56 Hz, 4H), 1.28 (s, 3H). HRMS calcd for C$_{16}$H$_{19}$BrCl$_2$N$_5$ (M+H)$^+$ 432.0155, found 432.0157. IC$_{50}$ is 0.169 μM.

To a solution of 6-(4-amino-4-methylpiperidin-1-yl)-3-(2,3-dichlorophenyl)pyrazin-2-amine (HCl salt) (15 mg, 0.043 mmol) in CH$_3$Cl (250 μL) was added at 0° C. and under N$_2$, NBS (7.58 mg, 0.043 mmol) in CH$_3$Cl (250 μL). After stirring for 2 h at RT the volatiles were removed under reduced pressure and the resulting residue was purified by HPLC (gradient elution 15-40% acetonitrile in water, 0.1% TFA modifier) to give the title compound (1.7 mg, 3.23 μmol, TFA salt). $^1$H NMR (400 MHz, METHANOL-d$_4$) δ ppm 7.53 (dd, J=8.03, 1.51 Hz, 1H), 7.31 (t, J=7.91 Hz, 1H), 7.24 (dd, J=7.65, 1.63 Hz, 1H), 3.74 (dt, J=13.87, 3.86 Hz, 2H), 3.10-3.18 (m, 2H), 1.84-1.97 (m, 2H), 1.72-1.84 (m, 2H), 1.39 (s, 3H). HRMS calcd for $C_{16}H_{19}Cl_3N_5$ (M+H)$^+$ 386.0706, found 386.0691. IC$_{50}$ is 0.392 µM.

Example 24

6-(4-amino-4-methylpiperidin-1-yl)-3-(2,3-dichlorophenyl)-5-methylpyrazin-2-amine

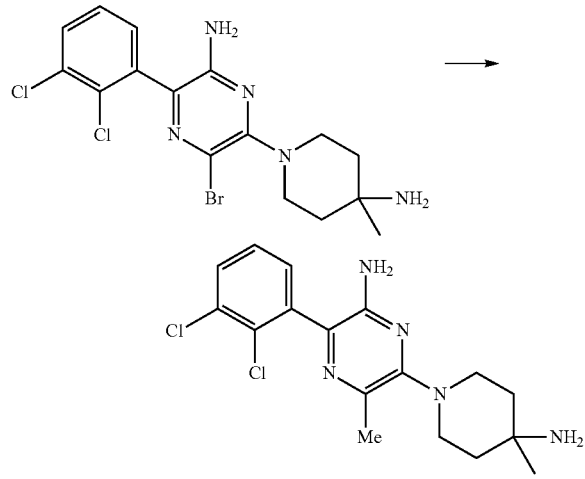

A suspension of 6-(4-amino-4-methylpiperidin-1-yl)-5-bromo-3-(2,3-dichlorophenyl)pyrazin-2-amine (20 mg, 0.046 mmol), potassium phosphate (29.5 mg, 0.139 mmol), PdCl$_2$(dppf).DCM adduct (1.9 mg, 0.002 mmol), and 2,4,6-trimethyl-1,3,5,2,4,6-trioxatriborinane (7.8 µL, 0.056 mmol) in MeCN:H$_2$O (9:1, 500 µL, degassed) was stirred in a microwave reactor for 1 h at 110° C. After cooling to RT, the volatiles were removed under reduced pressure and the resulting residue was purified by HPLC (gradient elution 25-50% acetonitrile in water, 5 mM NH$_4$OH modifier) to give the title compound (7.7 mg, 0.021 mmol). $^1$H NMR (400 MHz, METHANOL-d$_4$) δ ppm 7.52 (dd, J=8.03, 1.76 Hz, 1H), 7.31 (t, J=7.78 Hz, 1H), 7.23 (dd, J=7.65, 1.63 Hz, 1H), 3.25-3.15 (m, 2H), 3.01-3.13 (m, 2H), 2.25 (s, 3H), 1.51-1.74 (m, 4H), 1.14 (s, 3H). HRMS calcd for $C_{17}H_{22}Cl_2N_5$(M+H)$^+$ 366.1252, found 366.1248. IC$_{50}$ is 0.222 µM.

Example 25

5-amino-3-(4-amino-4-methylpiperidin-1-yl)-6-(2,3-dichlorophenyl)pyrazine-2-carbonitrile

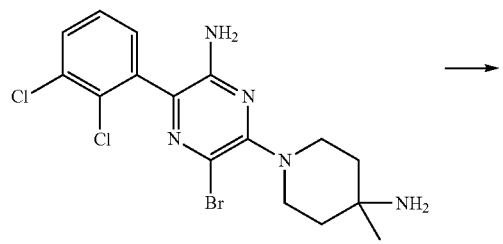

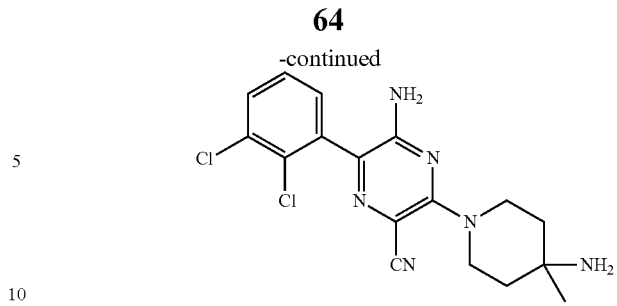

A solution of 6-(4-amino-4-methylpiperidin-1-yl)-5-bromo-3-(2,3-dichlorophenyl)pyrazin-2-amine (50 mg, 0.116 mmol) and copper(I) cyanide (20.8 mg, 0.232 mmol) in DMF (500 µL) was stirred in a microwave reactor for 2 h at 180° C. After cooling to RT, the reaction mixture was filtered and the resulting solution was purified by HPLC (gradient elution 25-50% acetonitrile in water, 5 mM NH$_4$OH modifier) to give the title compound (22.0 mg, 0.053 mmol). $^1$H NMR (400 MHz, METHANOL-d$_4$) δ ppm 7.64 (dd, J=7.96, 1.64 Hz, 1H), 7.42 (t, J=7.83 Hz, 1H), 7.35 (dd, J=7.58, 1.77 Hz, 1H), 3.83-4.04 (m, 2H), 3.62-3.83 (m, 2H), 1.58-1.79 (m, 4H), 1.25 (s, 3H). HRMS calcd for $C_{17}H_{19}Cl_2N_6$ (M+H)$^+$ 377.1048, found 377.1039. IC$_{50}$ is 0.315 µM.

Example 26

5-amino-3-(4-amino-4-methylpiperidin-1-yl)-6-(2,3-dichlorophenyl)pyrazine-2-carboxamide A solution of 5-amino-3-(4-amino-4-methylpiperidin-1-yl)-6-(2,3-dichlorophenyl)pyrazine-2-carbonitrile (38 mg, 0.101 mmol), NaOH (6 M in H$_2$O, 168 µL, 1.00 mmol), and hydrogen peroxide (103 µL, 1.00 mmol) in DMF (2 mL) was stirred in a microwave reactor for 1 h at 100° C. After cooling to RT, the reaction mixture was filtered and the resulting solution was purified by HPLC (gradient elution 15-40% acetonitrile in water, 0.1% TFA modifier) to give the title compound (12.8 mg, 0.034 mmol). $^1$H NMR (400 MHz, DMSO-d$_6$) δ ppm 7.65 (dd, J=7.53, 2.26 Hz, 1H), 7.36-7.46 (m, 2H), 7.32 (br. s., 1H), 6.91 (br. s., 1H), 6.23 (s, 2H), 3.37-3.52 (m, 4H), 1.50-1.75 (br. s, 2H), 1.36-1.53 (m, 4H), 1.08 (s, 3H). HRMS calcd for $C_{17}H_{21}Cl_2N_6O$ (M+H)$^+$ 395.1154, found 395.1140. IC$_{50}$ is 0.271 µM.

Example 27

3-(2,3-dichlorophenyl)-6-((3S,5R)-3,5-dimethylpiperazin-1-yl)pyrazin-2-amine

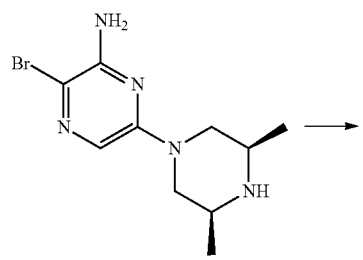

→ adduct (18.6 mg, 0.023 mmol) in MeCN:H$_2$O (9:1, 2.3 mL, degassed) was stirred in a microwave reactor for 1 h at 110° C. After cooling to RT, the volatiles were removed under reduced pressure and the resulting residue was purified by HPLC (gradient elution 25-50% acetonitrile in water, 5 mM NH$_4$OH modifier) to give the title compound (17.0 mg, 0.048 mmol). $^1$H NMR (400 MHz, METHANOL-d$_4$) δ ppm 7.74 (s, 1H), 7.59 (dd, J=7.78, 1.51 Hz, 1H), 7.45 (dd, J=7.78, 1.51 Hz, 1H), 7.38 (t, J=7.78 Hz, 1H), 3.56 (d, J=11.29 Hz, 2H), 3.03-3.21 (m, 2H), 2.44 (t, J=11.54 Hz, 2H), 1.17 (d, J=6.53 Hz, 6H). HRMS calcd for C$_{16}$H$_{20}$Cl$_2$N$_5$ (M+H)$^+$ 352.1096, found 352.1093. IC$_{50}$ is 0.570 μM.

The following compounds were made using the above procedure or modifications to the above procedure using the corresponding intermediate and boronic acid. Although in most cases the Boc protecting group was removed under the reaction conditions, HCl or TFA was used when necessary.

TABLE 4

| Example | Compound | Characterization | IC$_{50}$ (μM) |
|---|---|---|---|
| 28 | | $^1$H NMR (400 MHz, METHANOL-d$_4$) δ ppm 7.60 (d, J = 8.53 Hz, 2 H), 7.25-7.32 (m, 2 H), 7.10-7.16 (m, 1 H), 6.50-6.55 (m, 1 H), 3.77-3.87 (m, 2 H), 3.52-3.63 (m, 2 H), 1.60-1.75 (m, 4 H), 1.28 (s, 3 H). HRMS calcd for C$_{18}$H$_{22}$N$_6$ (M + H)$^+$ 323.1906, found 323.1977. | 0.632 |
| 29 | | as TFA salt. $^1$H NMR (400 MHz, DMSO-d$_6$) δ ppm 7.39 (s, 1 H) 5.91 (dt, J = 3.73, 2.05 Hz, 1 H) 5.55 (s, 2 H) 3.49-3.61 (m, 2 H) 3.42 (ddd, J = 13.01, 8.59, 4.17 Hz, 2 H) 2.22-2.31 (m, 2 H) 2.09-2.18 (m, 2 H) 1.52-1.72 (m, 4 H) 1.26-1.47 (m, 4 H) 1.06 (s, 3 H). HRMS calcd for C$_{16}$H$_{26}$N$_5$ (M + H)$^+$ 288.2188, found 288.2184. | 2.585 |

-continued

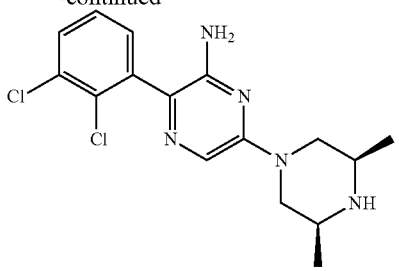

A suspension of 3-bromo-6-((3S,5R)-3,5-dimethylpiperazin-1-yl)pyrazin-2-amine (55 mg, 0.228 mmol), (2,3-dichlorphenyl)boronic acid (52.1 mg, 0.273 mmol), potassium phosphate (145 mg, 0.683 mmol), and PdCl$_2$(dppf).DCM

Example 30

3-(4-amino-4-methylpiperidin-1-yl)-6-(2,3-dichlorophenyl)-1,2,4-triazin-5-amine

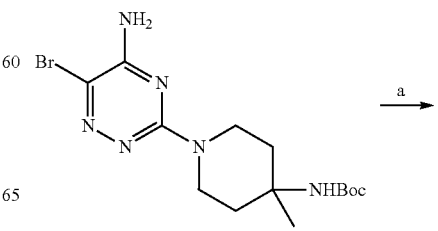

a →

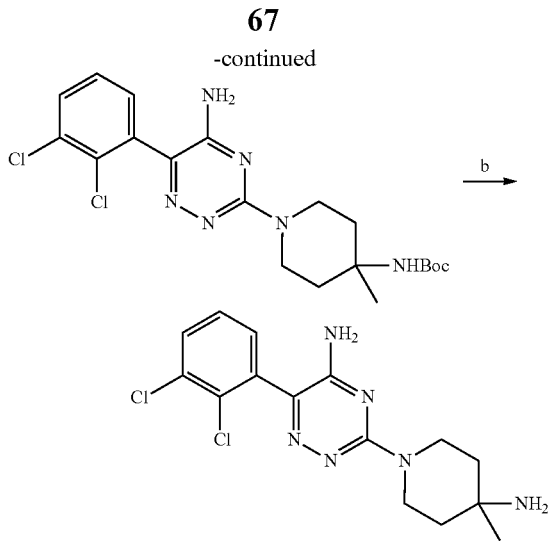

Step a: A suspension of (1-(5-amino-6-bromo-1,2,4-triazin-3-yl)-4-methylpiperidin-4-yl)carbamate (250 mg, 0.646 mmol), 2,3-dichlorophenylboronic acid (154 mg, 0.807 mmol), potassium phosphate (411 mg, 1.937 mmol), and XPhos $2^{nd}$ generation precatalyst (25.4 mg, 0.032 mmol) in MeCN:H$_2$O (9:1, 5 mL, degassed) was stirred in a microwave reactor for 2 h at 120° C. After cooling to RT, the reaction was filtered through a pad of Celite followed by EtOAc (20 mL) wash. The combined filtrates were concentrated and the resulting residue was purified by silica chromatography (0 to 5% gradient of MeOH (containing 1% NH$_3$)/DCM) to give tert-butyl (1-(5-amino-6-(2,3-dichlorophenyl)-1,2,4-triazin-3-yl)-4-methylpiperidin-4-yl)carbamate (78% purity). This mixture was further purified by HPLC (gradient elution 35-60% acetonitrile in water, 5 mM NH$_4$OH modifier) to give tert-butyl (1-(5-amino-6-(2,3-dichlorophenyl)-1,2,4-triazin-3-yl)-4-methylpiperidin-4-yl)carbamate (155 mg, 0.646 mmol). MS m/z 453.0 (M+H)$^+$.

Step b: To a solution of tert-butyl (1-(5-amino-6-(2,3-dichlorophenyl)-1,2,4-triazin-3-yl)-4-methylpiperidin-4-yl)carbamate (155 mg, 0.342 mmol) in dioxane (2 mL), was added HCl (4 M in dioxane, 4 mL). After stirring at RT until no starting material remained (monitored by LCMS, the volatiles were removed under reduced pressure and the resulting residue was purified by silica chromatography (0 to 5% gradient of MeOH (containing 1% NH$_3$)/DCM) to give the title (130 mg, 0.342 mmol, HCl salt). $^1$H NMR (400 MHz, METHANOL-d$_4$) δ ppm 7.80 (dd, J=7.78, 2.01 Hz, 1H), 7.42-7.58 (m, 2H), 4.29 (m., 2H), 3.64 (ddd, J=14.24, 9.47, 4.64 Hz, 2H), 1.92-2.06 (m, 4H), 1.57 (s, 3H). HRMS calcd for C$_{15}$H$_{19}$Cl$_2$N$_6$ (M+H)$^+$ 353.1048, found 353.1042. IC$_{50}$ is 0.194 µM.

Assays

Compounds of the invention were assessed for their ability to selectively inhibit SHP2 activity. The inhibitory properties of the compounds of the invention described herein can be evidenced by testing in any one of the following assays.

SHP2 Allosteric Inhibition Assay

SHP2 is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat#3575) using a final reaction volume of 25 µL and the following assay buffer conditions: 60 mM HEPES, pH 7.2, 75 mM NaCl, 75 mM KCl, 1 mM EDTA, 0.05% P-20, 5 mM DTT.

The inhibition of SHP2 by compounds of the invention (concentrations varying from 0.003-100 µM) was monitored using an assay in which 0.5 nM of SHP2 was incubated with of 0.5 µM of peptide IRS1_pY1172(dPEG8)pY1222 (sequence: H2N-LN(pY)IDLDLV(dPEG8)LST(pY)ASIN-FQK-amide) (SEQ ID NO:1). After 30-60 minutes incubation at 25° C., the surrogate substrate DiFMUP (Invitrogen, cat# D6567) was added to the reaction and incubated at 25° C. for 30 minutes. The reaction was then quenched by the addition of 5 µl of a 160 µM solution of bpV(Phen) (Enzo Life Sciences cat# ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized IC$_{50}$ regression curve fitting with control based normalization. IC$_{50}$ results for compounds of the invention are shown in examples and tables 1-7, above.

p-ERK Cellular Assay p-ERK cellular assay using the AlphaScreen® SureFire™ Phospho-ERK 1/2 Kit (PerkinElmer): KYSE-520 cells (30,000 cells/well) were grown in 96-well plate culture overnight and treated with Shp2 inhibitors at concentrations of 20, 6.6, 2.2, 0.74, 0.24, 0.08, 0.027 µM for 2 hrs at 37° C. Incubations were terminated by addition of 30 µL of lysis buffer (PerkinElmer) supplied with the SureFire phospho-extracellular signal-regulated kinase (pERK) assay kit (PerkinElmer). Samples were processed according to the manufacturer's directions. The fluorescence signal from pERK was measured in duplicate using a 2101 multilabel reader (Perkin Elmer Envision). The percentage of inhibition was normalized by the total ERK signal and compared with the DMSO vehicle control.

Colony Formation Assay and Cell Proliferation Assay

KYSE-520 Cells (1500 cells/well) were plated onto 24-well plates in 300 µL medium (RPMI-1640 containing 10% FBS, Lonza). For drug treatment, compounds of the invention at various concentrations (20, 10, 5, 2.5, 1.25 µM) were added 24 hours and 5 days after cell plating. At day 11, colonies were stained with 0.2% crystal violet (MP Biomedicals) and subsequently dissolved in 20% acetic acid for quantitation using a Spectramax reader (Thermo Scientific). In cell proliferation assay, cells (1500-cells/well) were plated onto 96-well plates in 100 µL medium (RPMI-1640 containing 10% FBS, Lonza). At day 6, 50 µL Celltiter-Glo reagent (Promega) was added, and the luminescent signal was determined according to the supplier's instruction (Promega).

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound of formula I:

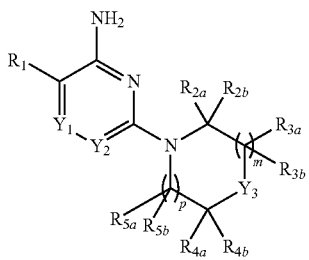

I in which:
m is selected from 0, 1 and 2;
p is 1;
$Y_1$ is selected from CH and N;
$Y_2$ is selected from $CR_6$ and N;
$Y_3$ is $CR_7R_8$;
$R_1$ is selected from $C_{6-10}$aryl, $C_{3-8}$cycloalkyl, $C_{3-8}$cycloalkenyl and a 5-9 member heteroaryl group containing from 1 to 4 heteroatoms selected from N, O and S;
  wherein said aryl or heteroaryl of $R_1$ is substituted with 1 to 5 $R_9$ groups independently selected from halo, amino, hydroxy, $N_3$, $C_{1-4}$ alkyl, $C_{1-4}$alkoxy, hydroxy-substituted-$C_{1-4}$alkyl, halo-substituted-$C_{1-4}$alkyl, amino-substituted-$C_{1-4}$alkyl, —C(O)O$R_{10}$ and —NHC(O)$R_{10}$;
$R_{10}$ is selected from hydrogen, phenyl and naphthyl;
  wherein said phenyl of $R_{10}$ is unsubstituted or substituted with methoxy;
$R_{2a}$ and $R_{2b}$ are independently selected from hydrogen, $C_{1-4}$alkyl, $C_{1-4}$alkoxy, amino, hydroxy, $C_{3-8}$cycloalkyl and $C_{1-4}$alkyl-amino;
$R_{3a}$ and $R_{3b}$ are independently selected from hydrogen, halo, carbonyl, $C_{1-4}$ alkyl, $C_{1-4}$alkoxy, amino, hydroxy, $C_{3-8}$cycloalkyl and $C_{1-4}$ alkyl-amino;
$R_{4a}$ and $R_{4b}$ are independently selected from hydrogen, halo, carbonyl, $C_{1-4}$ alkyl, $C_{1-4}$alkoxy, amino, hydroxy, $C_{3-8}$cycloalkyl and $C_{1-4}$alkyl-amino;
$R_{5a}$ and $R_{5b}$ are independently selected from hydrogen, carbonyl, $C_{1-4}$alkyl, $C_{1-4}$alkoxy, amino, hydroxy, $C_{3-8}$cycloalkyl and $C_{1-4}$alkyl-amino;
  wherein any two groups selected from $R_{2a}$, $R_{3a}$, $R_{4a}$ and $R_7$ can form a 5 to 6 member unsaturated, partially unsaturated ring or saturated ring optionally containing a ring nitrogen;
$R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$ alkyl, —S(O)$_{1-2}$$R_{6a}$, —C(S)$R_{6a}$, —C(O)N$R_{6a}$$R_{6b}$, —C(NH)N$R_{6a}$$R_{6b}$ and —N$R_{6a}$C(O)$R_{6b}$; wherein $R_{6a}$ and $R_{6b}$ are independently selected from hydrogen and $C_{1-4}$alkyl;
$R_7$ is selected from hydrogen, $C_{1-4}$alkyl, $C_{3-6}$cycloalkyl, $C_{6-10}$aryl and a 5-9 member heteroaryl group containing from 1 to 4 heteroatoms selected from N, O and S;
or $R_7$ and $R_{4a}$ together with the carbon atoms to which they are both attached can form a pyrrolidinyl or cyclopropyl group optionally substituted with amino;
$R_8$ is selected from amino, amino-methyl and methyl-amino;
or a pharmaceutically acceptable salt thereof.

2. The compound of claim 1 of Formula Ia:

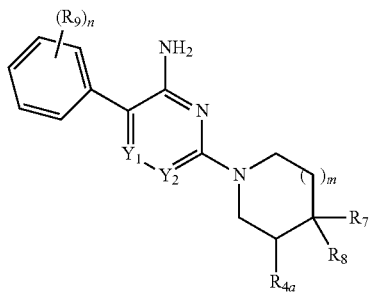

in which:
  m is selected from 0 and 1;
  n is selected from 1, 2, 3, 4 and 5;
  $Y_1$ is selected from CH and N;
  $Y_2$ is selected from $CR_6$ and N;
  $R_{4a}$ is selected from hydrogen, methyl and hydroxy;
  $R_6$ is selected from hydrogen, halo, cyano, $C_{1-4}$alkyl, $C_{1-4}$alkoxy, amino-carbonyl, halo-substituted $C_{1-4}$alkyl, halo-substituted $C_{1-4}$alkoxy, hydroxy-substituted $C_{1-4}$alkyl, amino-substituted $C_{1-4}$alkyl, —S(O)$_{1-2}$R$_{6a}$, —C(S)R$_{6a}$, —C(O)NR$_{6a}$R$_{6b}$, —C(NH)NR$_{6a}$R$_{6b}$ and NR$_{6a}$C(O)R$_{6b}$; wherein R$_{6a}$ and R$_{6b}$ are independently selected from hydrogen and $C_{1-4}$alkyl;
  $R_7$ is selected from hydrogen, methyl, phenyl, pyrazinyl and pyridinyl;
  or $R_7$ and $R_{4a}$ together with the carbon atoms to which they are both attached can form a cyclopropyl group substituted with amino;
  $R_8$ is selected from amino and methyl-amino;
  $R_9$ is selected from halo, amino, hydroxy, $N_3$, $C_{1-4}$alkyl, halo-substituted-$C_{1-4}$alkyl, $C_{1-4}$alkoxy, —C(O)OR$_{10}$ and —NHC(O)R$_{10}$;
  $R_{10}$ is selected from hydrogen, phenyl and naphthyl; wherein said phenyl of $R_{10}$ is unsubstituted or substituted with methoxy;

or a pharmaceutically acceptable salt thereof.

3. The compound of claim 2, or the pharmaceutically acceptable salt thereof, selected from:

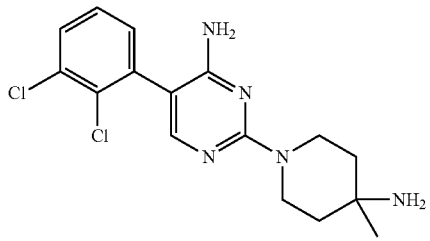

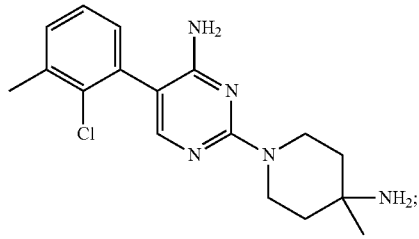

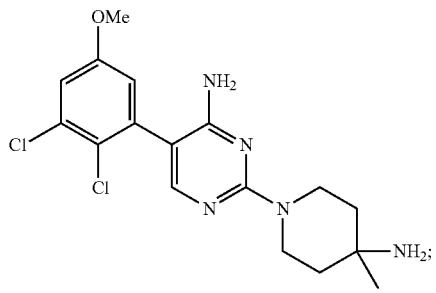

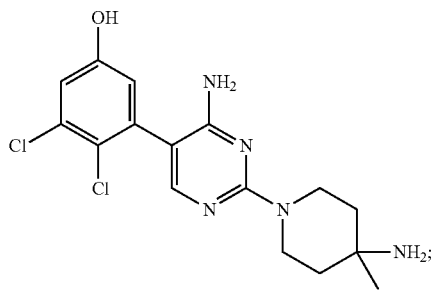

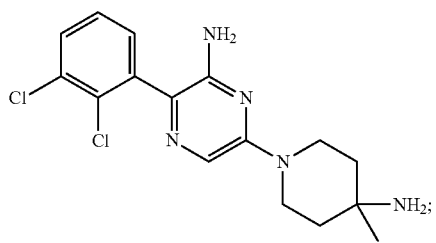

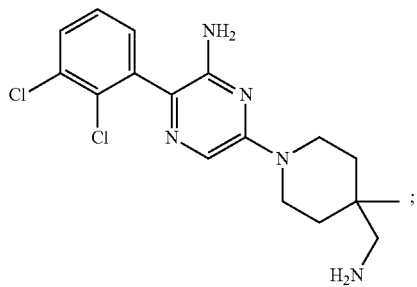

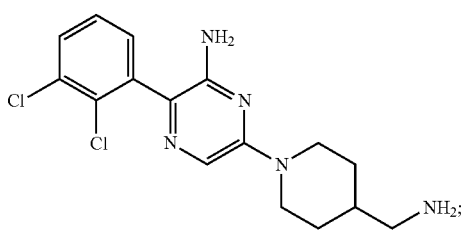

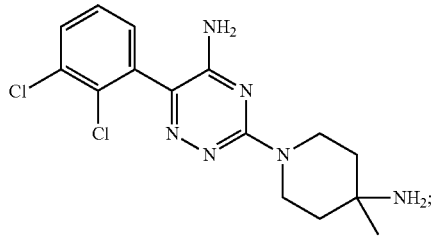

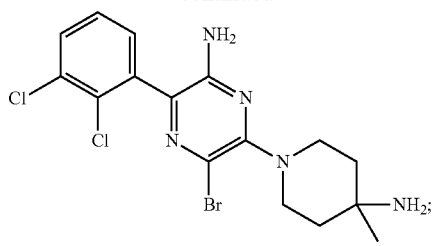
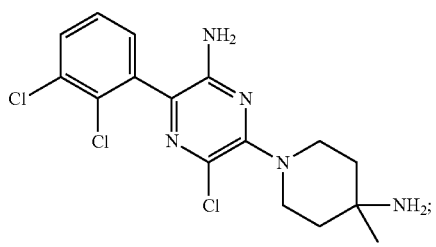
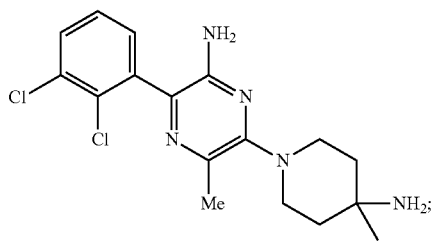
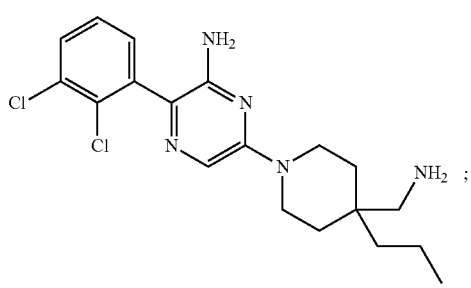
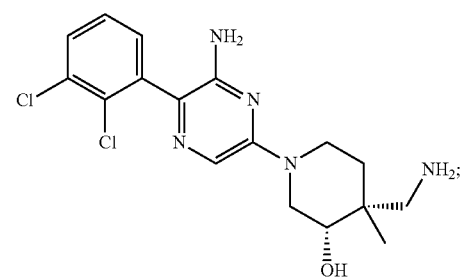
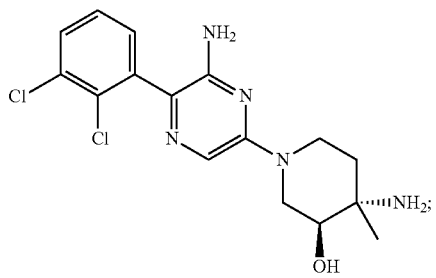
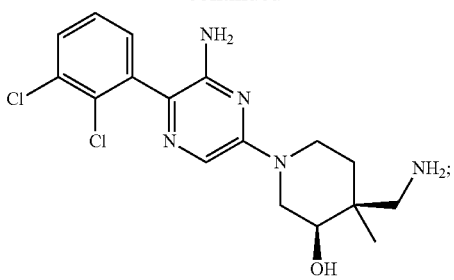
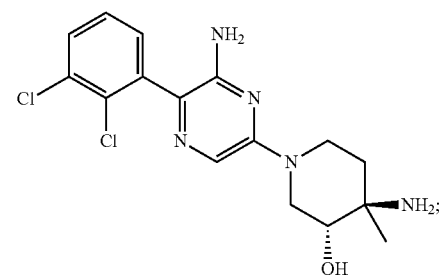
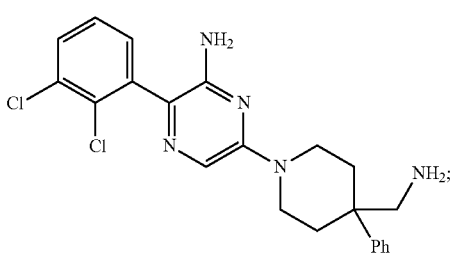
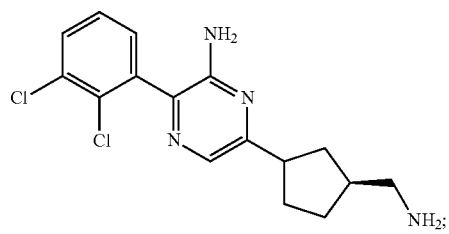
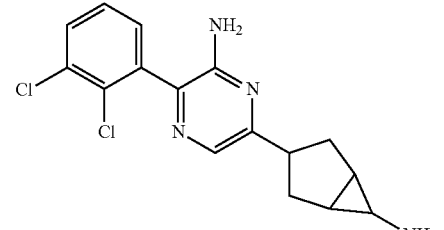
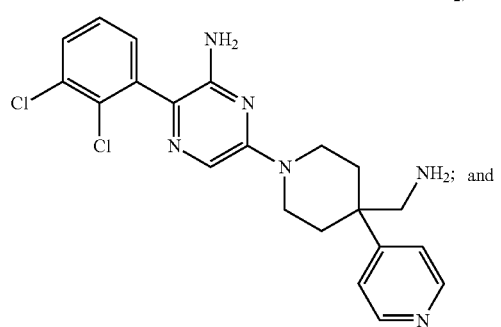

-continued

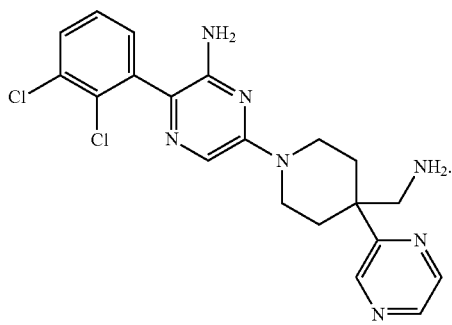

4. The compound of claim 1 of formula Ib:

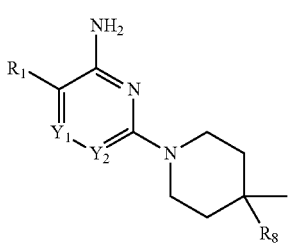

in which:
Y$_1$ is selected from CH and N;
Y$_2$ is selected from CR$_6$ and N;
R$_1$ is selected from thiophen-2-yl and 1H-indol-7-yl; wherein said thiophen-2-yl can be substituted with a group selected from methyl and chloro;
R$_6$ is selected from hydrogen, halo and methyl;
R$_8$ is selected from amino and methyl-amino;
or a pharmaceutically acceptable salt thereof.

5. The compound of claim 4, or the pharmaceutically acceptable salt thereof, selected from:

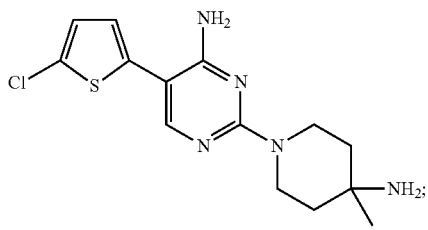

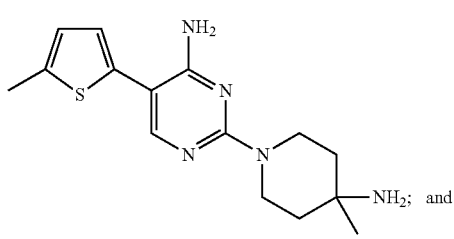

-continued

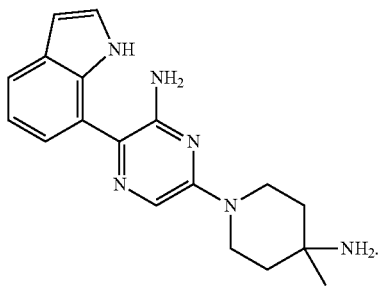 [SMILES: CC1(N)CCN(c2cnc(-c3cccc4cc[nH]c34)c(N)n2)CC1]

6. A compound of claim 1, wherein the compound is

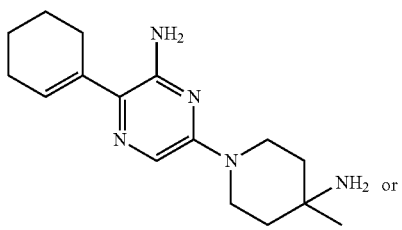

or a pharmaceutically acceptable salt thereof.

7. A compound of claim 1, or the pharmaceutically acceptable salt thereof, selected from:

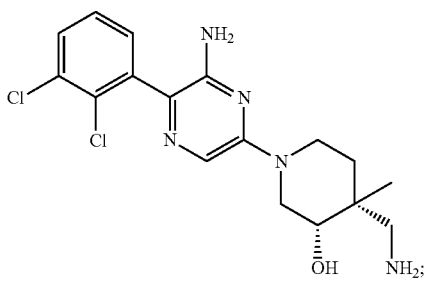

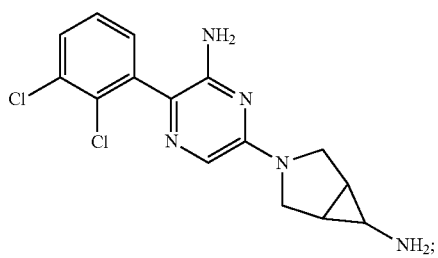

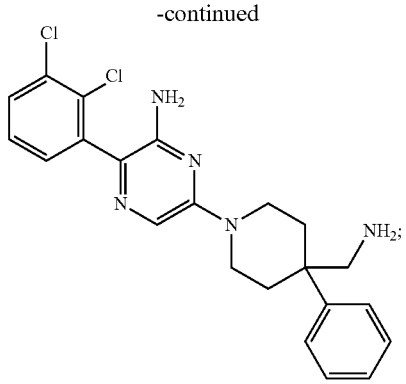
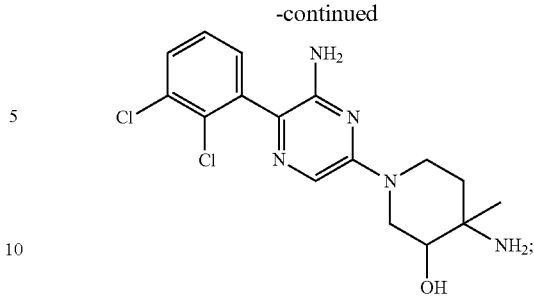

8. A pharmaceutical composition comprising a compound of claim 1 or a pharmaceutically acceptable salt thereof, and at least one pharmaceutically acceptable carrier.

9. A method of treatment comprising administering a compound of claim 1, or a pharmaceutically acceptable salt thereof, to a person in need of such treatment in an effective amount for the therapeutic treatment of a disease or disorder which is mediated by the activity of SHP2.

10. The method of claim 9, wherein the disease or disorder mediated by the activity of SHP2 is selected from Noonan Syndrome, Leopard Syndrome, juvenile myelomonocytic leukemias, neuroblastoma, melanoma, acute myeloid leukemia, breast cancer, esophageal cancer, lung cancer, colon cancer, head cancer, neuroblastoma, squamous-cell carcinoma of the head and neck, gastric carcinoma, anaplastic large-cell lymphoma and glioblastoma.

* * * * *